US011331343B2

(12) United States Patent
Nair et al.

(10) Patent No.: US 11,331,343 B2
(45) Date of Patent: May 17, 2022

(54) COMPOSITIONS AND METHODS FOR ACTIVATING ANTIGEN PRESENTING CELLS WITH CHIMERIC POLIOVIRUS

(71) Applicant: Duke University, Durham, NC (US)

(72) Inventors: Smita Nair, Durham, NC (US); Michael Brown, Durham, NC (US); Darell Bigner, Mebane, NC (US); Matthias Gromeier, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/321,144

(22) PCT Filed: Jun. 29, 2017

(86) PCT No.: PCT/US2017/039953
§ 371 (c)(1),
(2) Date: Jan. 28, 2019

(87) PCT Pub. No.: WO2018/005769
PCT Pub. Date: Jan. 1, 2018

(65) Prior Publication Data
US 2019/0167718 A1   Jun. 6, 2019

Related U.S. Application Data

(60) Provisional application No. 62/356,012, filed on Jun. 29, 2016.

(51) Int. Cl.
| | |
|---|---|
| *A61P 1/00* | (2006.01) |
| *A61P 35/00* | (2006.01) |
| *A61K 31/7105* | (2006.01) |
| *A61K 35/76* | (2015.01) |
| *A61K 39/00* | (2006.01) |
| *A61K 39/39* | (2006.01) |
| *A61K 45/06* | (2006.01) |
| *A61K 35/15* | (2015.01) |
| *A61K 9/00* | (2006.01) |
| *A61K 35/14* | (2015.01) |
| *C12N 5/0784* | (2010.01) |
| *A61P 31/00* | (2006.01) |

(52) U.S. Cl.
CPC .............. *A61K 35/15* (2013.01); *A61K 9/007* (2013.01); *A61K 9/0043* (2013.01); *A61K 9/0053* (2013.01); *A61K 31/7105* (2013.01); *A61K 35/14* (2013.01); *A61K 35/76* (2013.01); *A61K 39/0011* (2013.01); *A61K 39/39* (2013.01); *A61K 45/06* (2013.01); *A61P 31/00* (2018.01); *A61P 35/00* (2018.01); *C12N 5/0639* (2013.01); *A61K 2039/55561* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,622,705 A | 4/1997 | Morrow | |
| 5,817,512 A * | 10/1998 | Morrow | C12N 15/86 435/320.1 |
| 2003/0157135 A1* | 8/2003 | Tsuji | A61P 31/10 424/278.1 |
| 2006/0121003 A1 | 6/2006 | Gilboa et al. | |
| 2017/0087240 A1* | 3/2017 | Sanders | C12N 7/00 |

FOREIGN PATENT DOCUMENTS

| | | |
|---|---|---|
| JP | 2000-509281 A | 7/2000 |
| JP | 2016-500108 A | 1/2016 |
| WO | 9741210 A1 | 11/1997 |
| WO | 2014081937 A2 | 5/2014 |
| WO | 2014102220 A1 | 7/2014 |
| WO | 2016011422 A2 | 1/2016 |
| WO | WO-2016201224 A1 * | 12/2016 ............... C12N 7/02 |

OTHER PUBLICATIONS

May 27, 2020 (EP) Extended European Search Report—App. 17821238.7.
Brown et al. "Oncolytic poliovirus directs tumor antigen presentation and T cell activation in vitro" Journal for ImmunoTherapy of Cancer, Nov. 4, 2015, 3(Suppl 2):P332.
Lopez-Guerrero et al. "Poliovirus infection interferes with the phorbol ester-induced differentiation of the monocytic U937 cell line" Virus Research, 14 (Sep. 1, 1989) pp. 65-72.
Wahid et al. "Dendritic Cells and Macrophages Are Productively Infected by Poliovirus" Journal of Virology, vol. 79, No. 1, Jan. 1, 2005, pp. 401-409.
Hegmans et al. "Consolidative Dendritic Cell-based Immunotherapy Elicits Cytotoxicity against Malignant Mesothelioma" American Journal of Respiratory and Critical Care Medicine, vol. 181, No. 12, Jun. 15, 2010, pp. 1383-1390.
Crotty et al. "Protection against Simian Immunodeficiency Virus Vaginal Challenge by Using Sabin Poliovirus Vectors" Journal of Virology, vol. 75, No. 16, Aug. 15, 2001, pp. 7435-7452.
Sep. 21, 2017—International Search Report for International Application PCT/US2017/039953.
Gromeier et al. "Internal ribosomal entry site substitution eliminates neurovirulence in intergeneric poliovirus recombinants" PNAS, vol. 93, pp. 2370-2375, Mar. 1996.
Jan. 8, 2020—(JP) Office Action—Application No. 2018-568819.

\* cited by examiner

*Primary Examiner* — Nicole Kinsey White
(74) *Attorney, Agent, or Firm* — Banner & Witcoff, Ltd.

(57) ABSTRACT

Chimeric poliovirus is capable of activating antigen presenting cells. The activation of the antigen presenting cells may be in vitro, ex vivo, or in vivo. The activated antigen presenting cells may be administered alone or with an antigen or vaccine. The activated antigen may be loaded in vitro or ex vivo with antigen to form antigen-loaded, activated, antigen presenting cells. These may be administered therapeutically. Therapeutic administration of antigen presenting cells may be used as an adjuvant to other therapies.

34 Claims, 13 Drawing Sheets

Fig. 1. Genetic structure of PVSRIPO

COMPOSITIONS AND METHODS FOR ACTIVATING ANTIGEN PRESENTING CELLS WITH CHIMERIC POLIOVIRUS This application claims the benefit of U.S. Patent Application Ser. No. 62/356,012, filed Jun. 29, 2016. The contents of that patent application are expressly incorporated herein.

FIELD OF THE INVENTION

This invention relates to attenuated chimeric poliovirus capable of infecting and activating antigen presenting cells. More particularly it relates to therapeutic compositions and methods for adjuvanting an immune response.

BACKGROUND OF THE INVENTION

Antigen presenting cells (APCs), such as dendritic cells and macrophages, play an important role in the induction of innate immunity and adaptive immunity. Dendritic cells are the most potent APCs and coordinate T cell responses and B cell responses in an adaptive immune response. The stimulus for activation and maturation of dendritic cells, and the type of activation of the dendritic cell directly influence dendritic cell antigen presenting function, including the durability and type of an immune response induced by activated dendritic cells. Currently, dendritic cell vaccines involve enriching for $CD34^+$ precursor cells from the blood, incubating the cells in vitro with various cytokine combinations (e.g., TNFα and IL-3, GM-CSF, or GM-CSF and TNFα) for formation of immature dendritic cells; incubating immature dendritic cells in vitro with various cytokine cocktails (e.g., IL-1β, TNFα, IL-6 and $PGE_2$; or IFNγ; or $PGE_2$, TNFα, and a galactosylceramide) to generate mature dendritic cells; and incubating in vitro the mature dendritic cells with antigen to produce antigen-loaded dendritic cells comprising the dendritic cell vaccine.

There remains a need in the art for other means of activating dendritic cells and other antigen producing cells to produce vaccines which induce a potent and enduring adaptive immune response.

SUMMARY OF THE INVENTION

Antigen presenting cells, such as macrophages and dendritic cells, express poliovirus receptor (known as PVR, or Necl-5, or CD155) and are highly susceptible to infection by type 1 strains of poliovirus, and the Sabin 1 vaccine strain. Maximal cell-associated titers of virus occur within several hours post-infection. Cell death and lysis ensue (e.g., 24-36 hours post-infection). However, chimeric poliovirus, such as a Sabin type I strain of poliovirus with a foreign nucleotide sequence (i.e., from a source other than poliovirus) inserted in the 5' untranslated region of the poliovirus between its cloverleaf structure and open reading frame behaves differently. Surprisingly, it was discovered that, unlike wild-type type 1 poliovirus and the Sabin 1 vaccine strain which are cytopathogenic to antigen presenting cells that they infect, a chimeric poliovirus, as exemplified by PVSRIPO, infects and activates antigen presenting cells (including maturation) without cytotoxicity.

Methods and compositions are provided for activating antigen presenting cells.

Methods and compositions are provided for inducing an immune response using activated antigen presenting cells.

One aspect of the invention is a composition comprising activated antigen presenting cells, in vitro or ex vivo, in which the activated antigen presenting cells comprise a chimeric poliovirus. The chimeric poliovirus may optionally comprise a Sabin type I strain of poliovirus with a human rhinovirus type 2 internal ribosome entry site in the 5' untranslated region of the poliovirus between its cloverleaf structure and open reading frame. The activated antigen presenting cells may have been infected with the chimeric poliovirus, or transduced with RNA derived from the chimeric poliovirus.

One aspect of the invention is a method for activating antigen presenting cells, in vitro or ex vivo, comprising introducing into isolated antigen presenting cells a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. Introduction of the chimeric poliovirus into the antigen presenting cells may be by infection with the chimeric poliovirus as virus, or by transduction with RNA derived from the chimeric poliovirus. No maturation of the antigen presenting cells in a cytokine cocktail is required, as it is for previously known methods in the art for maturation of antigen presenting cells.

One aspect of the invention is a composition or combination comprising activated antigen presenting cells, and an antigen, wherein the activated antigen presenting cells comprise antigen presenting cells containing a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. The antigen may comprise an immunogen. The chimeric poliovirus may comprise infectious virus, or may comprise RNA isolated from the chimeric poliovirus.

One aspect of the invention is a composition for dermal delivery comprising an antigenic or immunogenic agent, and an adjuvant comprising a chimeric poliovirus. The chimeric poliovirus may comprise a Sabin type I strain of poliovirus with a human rhinovirus type 2 internal ribosome entry site in the 5' untranslated region of the poliovirus between its cloverleaf structure and open reading frame. The composition may further comprise a pharmaceutically acceptable carrier. A dermal delivery may optionally comprise a depot injection, optionally employing a pharmaceutically acceptable carrier that comprise an oil, emulsion, gel, semi-solid, viscous liquid, polymer, microparticles, or the like from which the composition is gradually absorbed by surrounding tissue. These carriers may prolong the time antigen presenting cells are exposed to the antigenic or immunogenic agent, as compared to an injection that is not a depot injection. The adjuvant, comprising the chimeric poliovirus, is capable of infecting antigen presenting cells, and activating them such that, in the presence of the antigen, an immune response is generated against the antigen (including an organism or cell bearing the antigen). The method of administering this composition dermally may vaccinate the recipient against the antigen.

One aspect of the invention is a method of eliciting an immune response to an immunogenic composition in an individual. The method comprises delivering an immunogenic composition into a dermal compartment of the skin of the individual. The immunogenic composition comprises an antigen and an adjuvant comprising a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. In one aspect, the immunogenic composition is a vaccine.

One aspect of the invention is an immunogenic composition comprising, as separate components which may then be formulated together to produce the immunogenic composition, an antigen and an adjuvant comprising a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. In one aspect, the immunogenic composition is a vaccine composition. The isolated immunogenic composition may be produced by combining its components ex vivo or in vitro.

One aspect of the invention is a kit comprising an immunogenic composition of the invention as described herein. In some aspects, the invention provides a kit comprising one or more containers filled with one or more of the components of the compositions of the invention, e.g., an antigen and/or an adjuvant comprising the chimeric poliovirus. In another aspect, the kit comprises two containers, one containing an antigen, and the other containing the adjuvant comprising the chimeric poliovirus. The kit may further comprise a dermal administration device and a dermal vaccine formulation. The kit may further comprise one or more components to facilitate reconstitution, administration, delivery, or use of the contents of the kit.

One aspect of the invention is a method of activating and antigen-loading antigen presenting cells. Antigen presenting cells are contacted with an antigen and a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. The chimeric poliovirus may comprise infectious virus (viral particles), or may comprise RNA derived from the chimeric poliovirus. The activated and antigen-loaded antigen presenting cells may be administered to an individual as a means of inducing an immune response in the individual or as a means of treating a disease to which the antigen relates.

One aspect of the invention is a method of treating an individual comprising administering to the individual an effective amount of an immunogenic composition. The immunogenic composition comprises an antigen and a chimeric poliovirus. In one aspect the chimeric poliovirus comprises a Sabin type I strain of poliovirus with a human rhinovirus type 2 internal ribosome entry site in the 5' untranslated region of the poliovirus between its cloverleaf structure and open reading frame. The chimeric poliovirus may comprise infectious virus, or may comprise poliovirus RNA derived from the chimeric poliovirus. In one aspect, the components of the immunogenic composition may be administered concurrently or sequentially. In one aspect, the treatment comprises vaccination. In another aspect, the immunogenic composition comprises a vaccine composition.

For the methods and compositions provided herein, the antigen may comprise a tumor antigen, or a pathogen antigen (e.g., bacterial antigen, parasite antigen, viral antigen), or an autoimmune disease antigen. Viral antigens in some embodiments are not poliovirus antigens, but rather antigens of other non-polio viruses.

For methods and compositions involving the treatment of an individual, the individual may be treated to prevent disease or treat a disease. The disease may be cancer, a pathogenic infection, a bacterial infection, a parasitic infection, a viral infection, or autoimmune disease. Typically the disease is not poliomyelitis.

For the methods in which compositions comprising antigen presenting cells are administered to an individual, the antigen presenting cells are, or are treated to be, compatible with the individual. Typically, the cells are autologous, but may be allogenic or otherwise made immunologically compatible.

One aspect of the invention is a method of eliciting, potentiating, or inducing an immune response, comprising an anti-tumor immune response, in an individual having or suspected of having a tumor, or at high risk of developing a tumor (e.g., as determined using a commercially available genetic test for predictive risk of tumor). The method comprises administering to the individual an effective amount of a composition comprising antigen presenting cells containing a chimeric poliovirus. In one aspect, the chimeric poliovirus comprises a Sabin type I strain of poliovirus with a human rhinovirus type 2 internal ribosome entry site in the 5' untranslated region of the poliovirus between its cloverleaf structure and open reading frame. The antigen presenting cells may further comprise antigen presenting cells which were loaded with tumor antigen (including tumor-associated antigen).

Other aspects, objects, and features of the invention will be apparent from the following description.

BRIEF DESCRIPTION OF THE DRAWINGS

FIG. 1 is a schematic of a chimeric poliovirus comprising a Sabin type I strain of poliovirus with a human rhinovirus type 2 internal ribosome entry site ("IRES") in the 5' untranslated region of the poliovirus between its cloverleaf structure("cloverleaf") and open reading frame ("ORF," solid black line).

DETAILED DESCRIPTION OF THE INVENTION

Figure 2A:
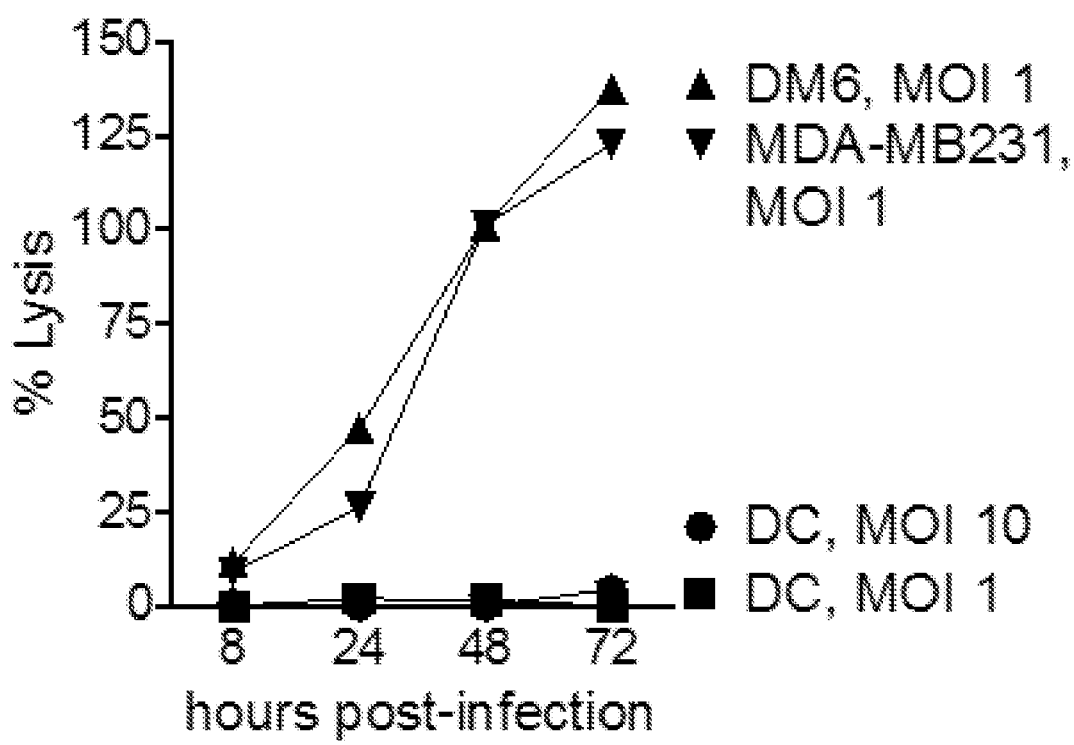
FIG. 2A is a graph showing percent lysis of human tumor cell lines DM6 (▲) and MDA-MB231 (▼) and human dendritic cells ("DC"; ●, ■) over 72 hours post infection with chimeric poliovirus at the designated multiplicity of infection (MOI).

While the terms used in the description of the invention are believed to be well understood by one of ordinary skill in the pharmaceutical arts, definitions, where provided herein, are set forth to facilitate description of the invention, and to provide illustrative examples for use of the terms.

As used herein, the terms "a," "an," and "the" mean "one or more," unless the singular is expressly specified (e.g., singular is expressly specified, for example, in the phrase "a single formulation").

As used herein, the terms "first" and "second" are for purposes of distinguishing between two compounds, or between two compositions, as will be clearer from the description.

As used herein, the term "kit" refers to a packaged combination of components, such as a chimeric poliovirus or an antigen; and may further comprise one or more components to facilitate reconstitution, administration, delivery, or use of the contents of the kit.

As used herein, the terms "eliciting," "potentiating," "promoting" or "inducing" are used to mean increasing, or mediating a treatment effect such as an immune response following treatment. For example, treatment with a composition provided herein may mediate, promote or induce a treatment effect which is greater than that when compared to monotherapy with a single component of the composition.

Chimeric polioviruses are any poliovirus which contains a segment from a human rhinovirus internal ribosome entry site in the 5' untranslated region of the poliovirus between its cloverleaf structure and open reading frame. Preferred such chimeric polioviruses are attenuated for safety and lack of neurovirulence, like the Sabin vaccine strain. The internal ribosome entry site may be from any human rhinovirus or other suitable virus. Also preferred is lack of cytotoxicity upon infection of antigen presenting cells, such as dendritic cells.

A virus may be administered to, delivered to, or contacted with a target cell using its naked genomic nucleic acid, its processed genomic nucleic acid, its transcriptome (consisting of mRNA), or its viral particle form. It appears that infection may be required to activate antigen presenting cells. However, if less than infection is required, the proteome of the chimeric poliovirus may be effective.

Any form of the viral RNA may be used to transfect cells. The RNA may be double stranded genome (replicative form), single stranded genome, or subgenomic RNAs. The RNA may be processed as an mRNA molecule. The RNA may have altered codons, for example, optimized codons, but still encode viral proteins. The RNA used in the methods may be RNA obtained from viral particles or RNA that is produced in cells that is not packaged into viral particles.

As used herein, the terms "dermal" and "dermally" with respect to administration or vaccination with a composition, is used to mean introduction into one or more layers or compartments of the skin. Such administration is typically into either the epidermis or the dermis, or between the epidermal and dermal layers. This could be done by administration via any method known in the art, including but not limited to, an injection process, or via topical application. Regarding topical application for example, using methods known in the art, a minor exfoliation process can remove the epidermal layer and generate enough inflammation to recruit DCs to the treatment area. A composition provided herein may then be applied topically to the treatment area in a process of vaccination or immunization or induction of an immune response provided herein. In one aspect, an immunogenic composition to be administered dermally is designed for targeted delivery of the immunogenic composition, preferably, selectively and specifically, to the intradermal compartment of an individual's skin.

Administration to the skin or to mucosa, whether in nose, stomach, lung, or intestines, for example, may be accomplished in a direct or targeted manner. Such administration is not systemic, but rather may involve direct instillation of a medicament (such as a chimeric poliovirus) at the target site in the body. It may, alternatively involve topical, intradermal, or subcutaneous administrations. Direct or targeted administrations may be accomplished, for example, by a nasal spray, by endoscopy, or bronchoscopy. Other sites in the body that have antigen presenting cells, in particular dendritic cells, may also be targeted. For accessing antigen presenting cells in the blood, a medicament such as chimeric poliovirus or a medicament made using chimeric poliovirus may be administered systemically. Systemic administration may be used to access multifocal or metastatic lesions, for example. Other disseminated diseases may also be treated in this manner.

As used herein, the term "pharmaceutically acceptable carrier" means any compound or composition or carrier medium useful in any one or more of administration, delivery, formulation, storage, stability of a composition or combination described herein. These carriers are known in the art to include, but are not limited to, a diluent, water, saline, suitable vehicle (e.g., liposome, microparticle, nanoparticle, emulsion, capsule), buffer, tracking agents, medical parenteral vehicle, excipient, aqueous solution, suspension, solvent, emulsions, detergent, chelating agent, solubilizing agent, salt, colorant, polymer, hydrogel, surfactant, emulsifier, penetrant, adjuvant, filler, preservative, stabilizer, oil, binder, disintegrant, absorbant, flavor agent, and the like as broadly known in the pharmaceutical art.

As used herein, the terms "cancer" or "tumor" refer to all types of cancer, neoplasm or malignant tumors found in mammals (e.g., humans), including, but not limited to, leukemia, lymphomas, carcinomas and sarcomas. Tumor antigens are those which are specifically associated with higher levels of expression on tumors than on surrounding normal tissue. Alternatively, tumor antigens that are used may be antigens that are uniquely present in the tumors, such as those created by a somatic mutation in the tumor. Other useful tumor antigens may be viral antigens that are expressed in tumors that are caused by viruses, such as HPV.

As used herein, the term "individual" is used to refer to a mammal, preferably a human, or a human in need of the composition, method, treatment, or medicament described herein. In some embodiments that human does not have a brain tumor.

As used herein, the term "antigen" is herein to refer to a molecule capable of inducing an immune response. In one aspect, the molecule may comprise an immunogen. The molecule may be polysaccharide, carbohydrate, lipid, protein (e.g., protein, glycoprotein, lipoprotein, fragment thereof (peptide) or recombinant protein), or a nucleic acid molecule encoding an antigen (e.g., DNA, RNA, mRNA, expression vector). The antigen may be an antigen from a bacterial species, including but not limited to an antigen from Mycobacterial species (such as *Mycobacteria tuberculosis* or species containing cross-reactive antigens therewith such as BCG) (e.g., 32A, 39A, Ag85A, Ag85B, and TB10.4), and an antigen from *Borrelia* species (e.g., *Borrelia burgdorferi*, and *Borrelia mayonii, Borrelia afzelii*, and *Borrelia garini*) (e.g., outer surface protein A (OspA) OspB, OspC, DpbA, and Bbk32), irradiated or heat-inactivated bacteria, and chemically-inactivated bacteria. The antigen may be from a virus, including but not limited to an antigen from human immunodeficiency virus (e.g., gp120, gp41, tat, vif, rev, vpr), an antigen from respiratory syncytial virus (e.g., F glycoprotein, G glycoprotein), an antigen from influenza virus (e.g., neuraminidase, hemagglutinin), an antigen from herpes simplex virus (e.g., glycoproteins such as gB, gC, gD, and gE), an antigen from papillomavirus (e.g., L1, E6, E7), an antigen from a hepatitis virus (A, B, C), an antigen from zika virus (e.g., NS-1, E), an antigen from Chikungunya virus (e.g., NS1, E1, E2, C)), irradiated or heat-inactivated virus, and chemically-inactivated virus. The antigen may be from a parasite, including but not limited to, an antigen from a Plasmodium species (e.g., MSP-1, CSP, TRAP, CyRPA), irradiated or heat-inactivated parasite, and chemically-inactivated parasite. The antigen may be a tumor antigen that comprises: a product of a mutated gene; a cell surface protein overexpressed or aberrantly expressed on tumor cells; a products of an oncogenic virus; an oncofetal antigen; a cell surface glycolipid or glycoprotein with aberrant glycosylation; a tumor cell lysate (oncolysate); a shed tumor antigen (e.g., collected from and shed into cell culture medium of cultured tumor cells, or from body fluid surrounding a tumor), exosomes from tumor cells; RNA purified from tumor cells; or nucleic acid molecules encoding a tumor antigen. Examples of such antigens are well known in the art to include MUC-1, alpha fetoprotein, ovarian carcinoma antigen (CA125), carcinoembryonic antigen (CEA), Lewis antigens, ganglioside N-glycolyl-$GM_3$, tyrosinase, melanoma-associated antigen (MAGE), EGFRviii, RAGE-1, HER2 (human epidermal growth factor receptor 2), and Melan-A/MART-1. In light of dendritic cells ability to migrate into the central nervous system, an antigen may comprise an antigen associated with an autoimmune disease such as a neuroinflammatory disease such as Alzheimer's disease (e.g., peptides $A\beta_{1-42}$, $A\beta_{1-6}$, $A\beta_{1-42}$. Tau-peptide $C_{-294-305}$, AV-1959R, AV-1980R, AV-1953R). The antigen to be used is typically not one which is part of poliovirus or the Sabin strain of poliovirus or the chimeric poliovirus known as PVSRIPO.

As used herein, the term "antigen loading" is used to refer to a process by which an antigen and antigen presenting cells are contacted with each other, and promoted is uptake of an antigen into the antigen presenting cell for further processing by the antigen presenting cell. Techniques for antigen loading are known to those skilled in the art to include, but are not limited to, pulsing (e.g., through contact or incubation with) dendritic cells with antigen; and electroporating, transfecting, transducing or otherwise introducing DNA or RNA or mRNA encoding antigen, and immune complex loading (antigen bound to antibody having binding specificity therefor).

As used herein, the term multiplicity of infection or "MOI" refers to the number of virions that are added per cell during infection. For example, if one million virions are added to one million cells, the MOI is one. Sublethal doses (MOI) are those that do not induce cytotoxicity in the target cells. Sublethal doses may be used to accomplish the activation employed in the methods. What the precise level is may vary from chimeric virus to chimeric virus and may further vary with cell type. However, determination of a sublethal level is well within the skill of the ordinary artisan using simple methods known in the art. In some embodiments a lethal level may be an MOI greater than 1, greater than 10, or greater than 100. In some embodiments a sublethal level may be an MOI of less than 1, less than 0.5, less than 0.1, less than 0.05, or less than 0.01.

The term "dendritic cell," is known in the art to mean an antigen-presenting cell (APC) capable of inducing an immune response upon activation. The dendritic cells may comprise isolated dendritic cells, which may be a composition enriched for dendritic cells or containing purified dendritic cells, isolated from any source containing dendritic cells, such as nonlymphoid organs, peripheral blood, skin, and other tissues, including mucosa from lung, stomach, nose, and intestine. Dendritic cells are comprised of at least three distinct subpopulations, two in the myeloid lineage and one in the lymphoid/plasmacytoid lineage. Myeloid dendritic cells are found in most nonlymphoid organs including the dermis, epidermis (termed "Langerhans cells"), gastrointestinal mucosa, respiratory mucosa, and the interstitia of vascular organs. When referring to dermal dendritic cells or skin dendritic cells, Langerhans cells (typically $CD1_o^{high}$), $CD141^{high}$ dermal dendritic cells, and $CD1c^+$ dendritic cells are included. Plasmacytoid dendritic cells circulate in the blood and are found in peripheral lymphoid organs. They constitute less than 0.4% of peripheral blood mononuclear cells, and develop from bone marrow hematopoietic stem cells. Dendritic cells express CD155, the receptor for poliovirus infection. After exposure to an inflammatory stimulus, dendritic cells undergo phenotypic and functional changes that characterize their transition from immature to mature dendritic cells. In that regard, dendritic cell activation and maturation is characterized by upregulation of costimulatory molecules CD40, CD80, CD86, increased cell surface expression of HLA classes I and II, and upregulation of the specific dendritic cell marker CD83. Increased expression of costimulatory molecules, such as CD80 CD86, amplify T cell receptor (TCR) signaling and promote T cell activation. The process of dendritic cell maturation also involves secretion of chemokines, cytokines and proteases, and surface expression of adhesion molecules and chemokine receptors. For example, dendritic cells rapidly begin to produce IL-12, a signal that helps direct naive CD4 T cells towards a Th1 phenotype. Modulation of chemokine responsiveness and production is also responsible for the ability of activated dendritic cells to migrate from the peripheral tissues into secondary lymphoid tissues and organs where activated dendritic cells exert their antigen presenting functions and provide a crucial step in the development of adaptive immunity. Antigen presenting cells such as but not limited to dendritic cells may be isolated from a tissue or body fluid, and then activated using an adjuvant or immunogenic composition described herein. Other antigen presenting cells may be used, whether professional antigen presenting cells or nonprofessional. Professional antigen presenting cells include macrophages and B cells.

As used herein, the term "immune response" in reference to an antigen or composition is the development in an individual of an immune response to an antigen, or antigen present in the composition. The immune response elicited may be selected from the group consisting of a humoral immune response, a cellular immune response, an adaptive immune response, and a combination thereof. Methods of treatment provided herein for eliciting an immune response may be referred to as immunotherapy. Compositions provided herein for eliciting an immune response may be referred to herein as immunogenic compositions.

As used herein, the terms "treat," "treating," or "treatment" embrace one or more of preventative (prophylactically) or therapeutically (palliative) procedures. An individual treated for a pathogenic disease or infectious disease, includes but is not limited to treatment of an infection caused by a pathogen selected from the group consisting of bacteria, virus, parasite, and a combination thereof.

As used herein, an "effective amount" means an amount of a composition or combination which results in a desired treatment effect following administration to an individual in need of such composition or combination. In immunotherapy, the treatment effect may be represented by induction of an immune response. Such induction may be measured, depending on the type or types of immune response induced (e.g., humoral and/or cellular immune response) by an increase in antibody titer, an increase in one or more T cell subpopulations (e.g., $CD4^+$ T cells, $CD8^+$ T cells), an increase in activated dendritic cells or change in other relevant cell population (e.g., B cells, macrophages) which can be measured using methods known in the art (e.g., labelling with detectable markers followed by immunoassay or flow cytometry analyses). Alternatively, the immune response may also be measured by a decrease in number or function of regulatory T cells (e.g., $CD25^+$ $FoxP3^+$, $CD4^+$ cells). Thus, in one aspect, treatment efficacy may be assessed by clinical outcome; an increase in the number of activated T cells as compared with the number prior to treatment or in absence of treatment, an increase in serum titer of antibodies against an antigen, etc. In treatment of cancer, a therapeutic effect may include but is not limited to, one or more of (a) an immune-related response, as known to those skilled in the art as an immune-related complete response or an immune-related partial response relative to total tumor burden; and (b) traditional overall objective response rate using the appropriate response assessment criteria known to those skilled in the art and depending on the type of cancer treated (e.g., for lymphoma, see Cheson et al., 2014, *J. Clin. Oncology* 32 (27):3059-3067; for solid nonlymphoid tumors, Response Evaluation Criteria In Solid Tumors (RECIST)).

In any of the compositions and methods of treatment provided herein, the dosage of or amount of antigen and of the chimeric poliovirus will depend on such factors as the mode of administration, the formulation for administration, type of immunotherapy, immunogenicity of antigen, the size, health, and immunocompetence of the individual to receive such a composition, and other factors which can be taken into consideration by a medical practitioner whom is skilled in the art of determining appropriate dosages for treatment. For example, for methods of treatment provided herein, the chimeric poliovirus may be administered in a dosage range of from about $1 \times 10^4$ TCID to about $1 \times 10^{10}$ TCID (tissue culture infectious dose), or in a MOI ranging from about 0.01 to about 10. One skilled in the art can apply known principles and models of drug delivery and pharmacokinetics to ascertain a likely range of dosages to be tested in preclinical and clinical studies for determining a therapeutically effective amount of a composition or combination used in the methods of treatment provided herein. A composition or combination, useful in a method of treatment provided herein, may further comprise a pharmaceutically acceptable carrier to facilitate one or more of storage, formulation stability, administration, and delivery. The carrier may be particulate, so that the composition or combination may be in, for example, powder or solid form. The carrier may be in a semi-solid, gel, or liquid formula, so that the composition or combination may be injected, applied, or otherwise administered. The mode of administration of a composition or combination, useful in a method of treatment provided herein, to an individual (such as a human) in need of thereof may be any mode known in the art to be suitable for delivering a pharmaceutical composition, and particularly suitable for treatment by immunotherapy. Depending on the type of immunotherapy, administration may include but is not limited to, intratumoral, dermal, intradermal, intracavitary, intravenous, intraperitoneal, subcutaneous, intramuscular, intranasal, by perfusion, and by peristaltic techniques.

The frequency, order of administration, doses and dosage regimen for compositions described herein can be determined by a physician, taking into account the medical literature, the health, age and sex of the individual, type of immunotherapy, the mode of administration and dosing schedule of the composition or combination or therapy, and other relevant considerations. In a method of treatment provided herein, an immunogenic composition may be administered to an individual at a suitable frequency to be effective in inducing an immune response. For example, immunization or vaccination may be one administration, or a series of administrations. For example, the chimeric poliovirus may be administered once, administered at the same frequency as an antigen, or administered at a different frequency as an antigen. In a method of treatment using an immunogenic composition provided herein, in one example, administration of an antigen is preceded by administration of a chimeric poliovirus. In another example of a method of treatment using an immunogenic composition provided herein, administration of an antigen is simultaneous or concurrent with administration of a chimeric poliovirus. In another example of a method of treatment using an immunogenic composition provided herein, administration of an antigen precedes administration of a chimeric poliovirus.

EXAMPLE 1

Figure 1:
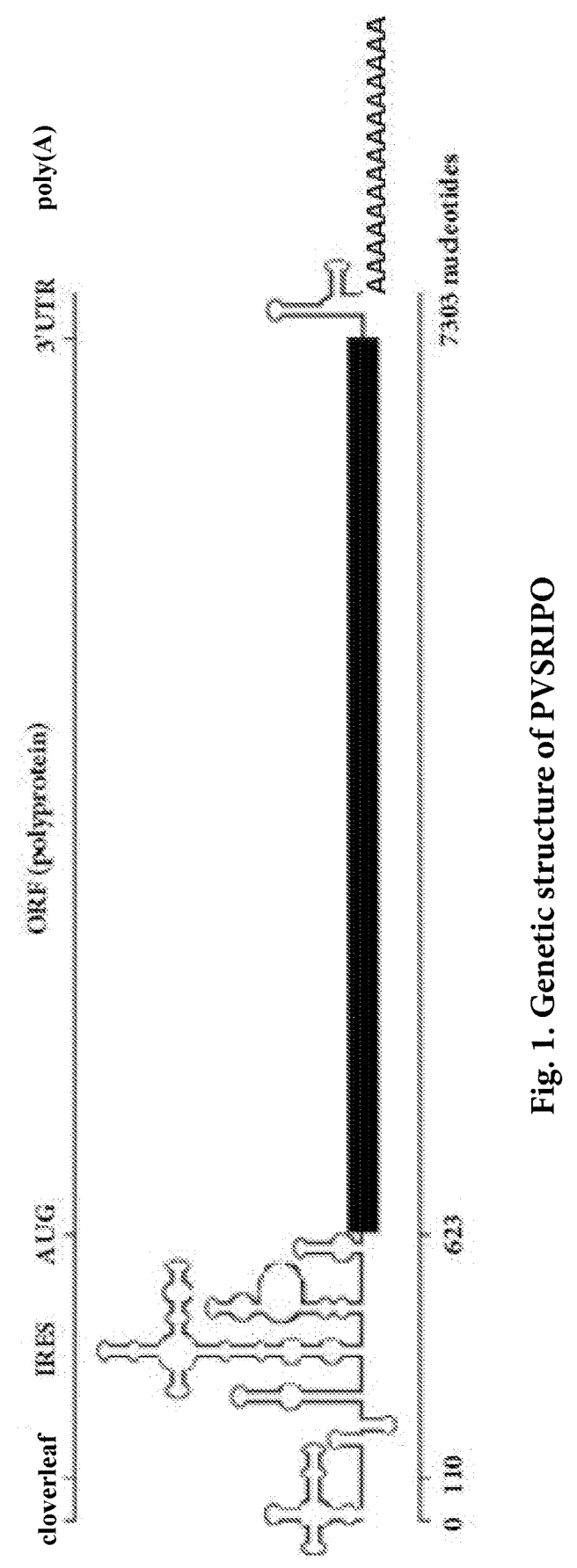

FIG. 1 shows the construct of a chimeric poliovirus comprising a Sabin type I strain of poliovirus with a human rhinovirus type 2 internal ribosome entry site in the 5' untranslated region of the poliovirus between its cloverleaf structure and open reading frame. This illustrated chimeric poliovirus, also known as PVSRIPO, has shown efficacy in treating tumor expressing poliovirus receptor (CD155) in Phase I trials of individuals with recurrent glioblastoma. For example, individuals with recurrent glioblastoma treated with PVS-RIPO have a 36-month survival rate (95% confidence interval) of 21.1% as compared to 4% for historical controls of recurrent glioblastoma (as of Mar. 1, 2017). There are two individuals which appear to have no evidence of recurrent tumor five years after treatment. Methods of manufacturing chimeric poliovirus, including but not limited to PVS-RIPO, are known in the art (see for example, WO2016/201224). Thus, chimeric poliovirus has demonstrated safety in treatment of individuals, particularly in humans, and has been successfully manufactured according to GMP and FDA specifications.

Isolation of dendritic cells. Immature dendritic cells can be isolated form tissue or peripheral blood using methods known in the art. For use in the examples illustrated herein, immature dendritic cells were generated as follows. Peripheral blood mononuclear cells (PBMCs) were isolate from human blood and then frozen. Frozen PBMCs were thawed, washed in phosphate-buffered saline (PBS), and resuspended at $2\times10^8$ cells in culture medium in T-150 culture flasks. Cells were incubated for 1 hour at 37° C. in a 5% $CO_2$ incubator. Non-adherent cells were harvested by rocking the culture flask from side to side to dislodge them. The adherent cells were replenished with 30 ml of culture medium containing 800 U/ml of human GM-CSF and 500 U/ml of IL-4 and then incubated at 37° C. After a 7-day culture period, loosely adherent clusters of DCs were dislodged by firmly tapping the flasks. Adherent DCs were washed with cold PBS, treated with dissociation buffer and incubate at 37° C. for 15-20 minutes, and harvested by firmly tapping the flasks followed by vigorous pipetting. The harvested DC preparations were the combined, washed, pelleted, and resuspended to result in a preparation of immature DCs. Immature DCs were shown to be CD155+ by flow cytometric staining and analyses.

Infection of dendritic cells with chimeric poliovirus. Antigen presenting cells expressing CD155 are susceptible to a virus-producing and lethal infection by poliovirus. Infection of tumor cells expressing CD155 with chimeric poliovirus (e.g., PVSRIPO) produces a lethal infection, resulting in oncolysis. Thus, it was unexpected that infection of antigen presenting cells, such as dendritic cells and macrophages, with chimeric poliovirus (e.g., PVSRIPO) does not result in a lethal infection (infected dendritic cells are not killed by chimeric poliovirus), as shown in this example. Further, infection of DCs with chimeric poliovirus resulted in activation of the infected DCs, as shown herein in Example 2.

In this example, $CD155^+$ human tumor cell lines DM6 (Duke Melanoma 6) and MDA-MB231 (human breast adenocarcinoma), and immature human DCs were each infected with chimeric poliovirus. Five hundred thousand cells were plated in 35 mm dishes, and infected at the designated multiplicity of infection ("MOI"; as shown in FIG. 2) by adding chimeric poliovirus (PVSRIPO) to the cell culture medium. At 8 hours, 24 hours, 48 hours, and 72 hours post-infection, the cells were analyzed for cell lysis and for virus production. Cell lysis was evaluated by measuring the amount of lactate dehydrogenase (LDH) in the medium using a colorimetric assay (LDH is an intracellular enzyme released into the medium of cultured cells only upon cell death; i.e., LDH is used as a cell death marker). For measurement of virus production, plaque forming units were determined using a standard plaque assay using methods known in the art.

Figure 2B:
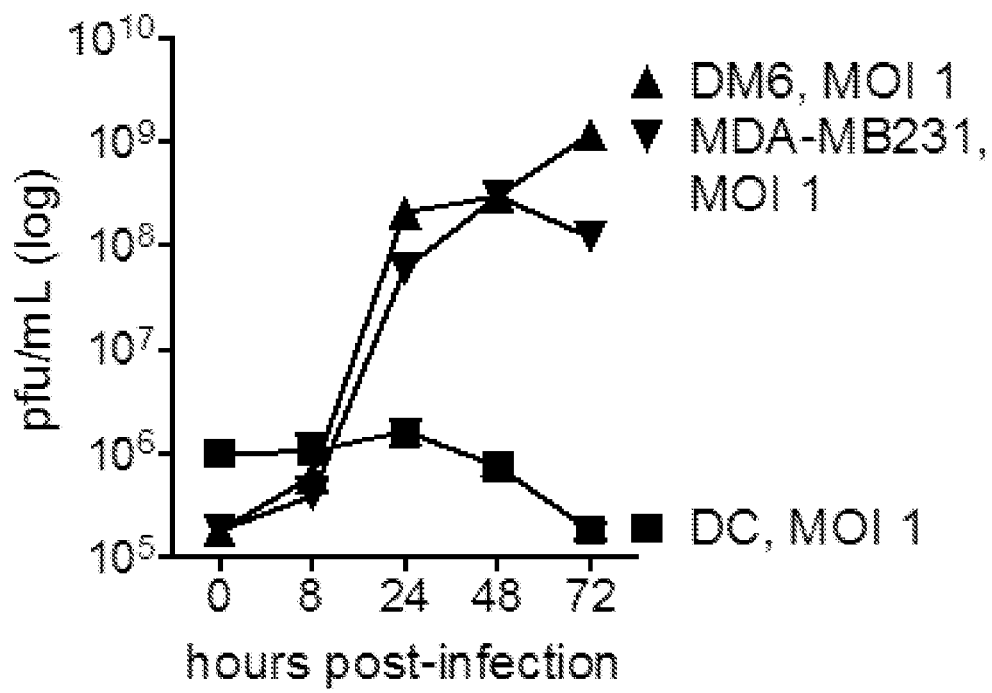
FIG. 2B is a graph showing virus production (plaque forming units; pfu) of human tumor cell lines DM6 (▲) and MDA-MB231 (▼) and human dendritic cells ("DC"; ■) over 72 hours post infection with chimeric poliovirus at the designated multiplicity of infection (MOI).
Figure 2C:
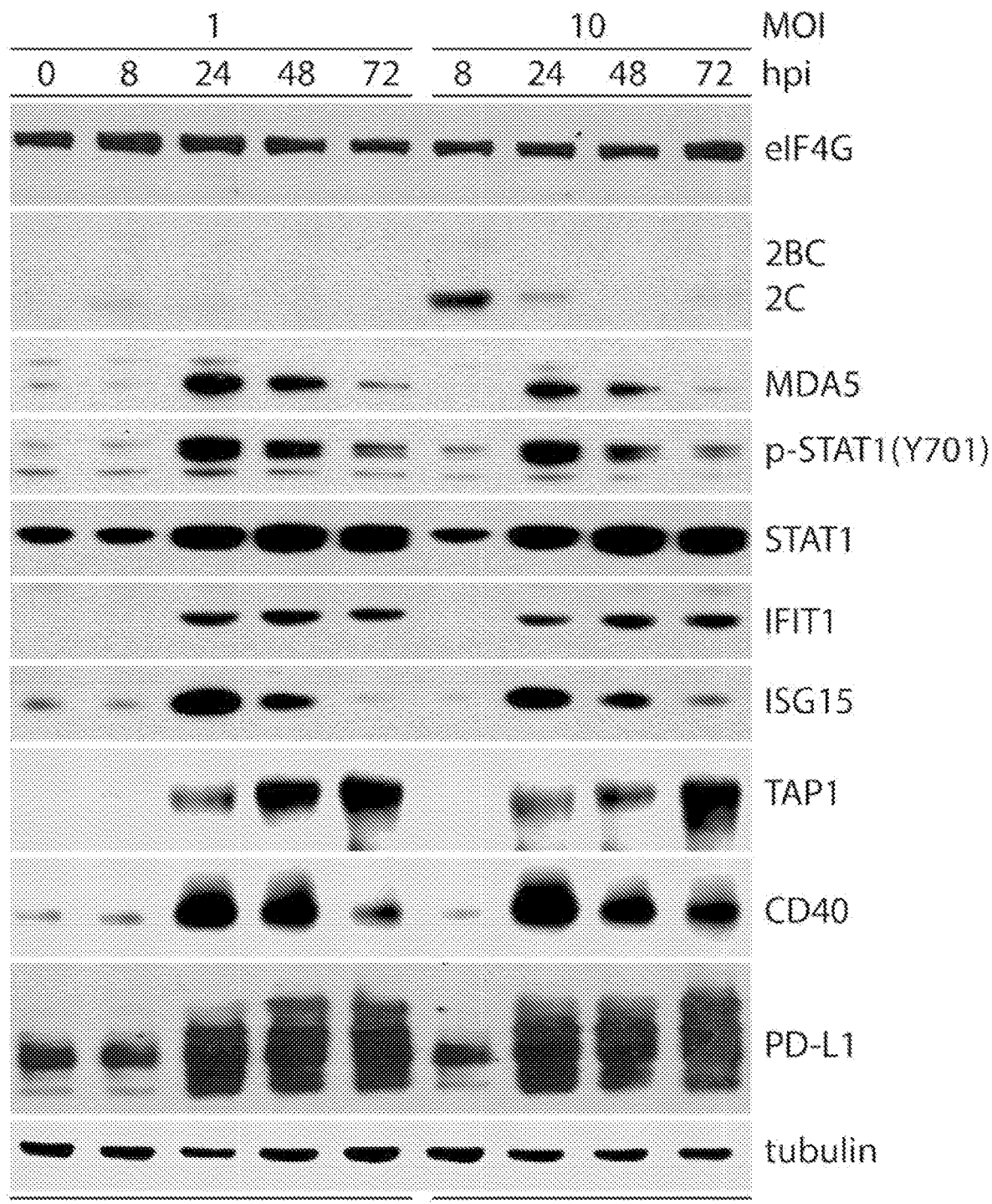
FIG. 2C is an immunoblot of human dendritic cells showing expression of various proteins (eIF4G, 2BC, 2C, MDA5, p-STAT1(Y701), STAT1, IFIT1, ISG15, TAP1, CD40, PD-L1, and tubulin) at 8, 24, 48, and 72 hours post infection with chimeric poliovirus.
Figure 3A:
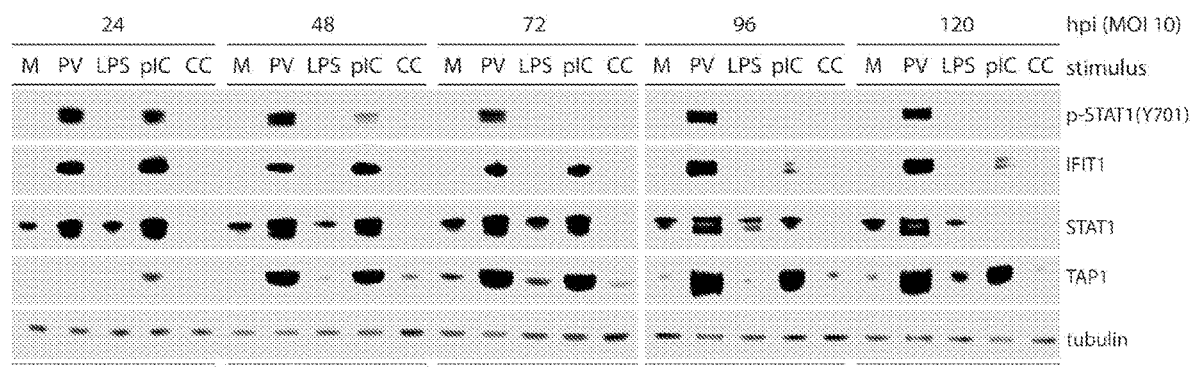
FIG. 3A is an immunoblot of human dendritic cell lysates showing expression of various proteins (p-STAT1(Y701), STAT1, IFIT1, TAP1, and tubulin) at 8, 24, 48, 72, 86, and 120 hours following no treatment (M), or treatment with chimeric poliovirus ("PV"; MOI=10), or LPS (100 ng/ml), or poly(I:C) ("pIC," 10 µg/ml), or maturation cytokine cocktail ("CC," TNF-α, 10 ng/ml; IL-1β, 10 ng/ml; IL-6, 1000 U/ml; and PGE$_2$, 1 µg/ml).
Figure 3B:
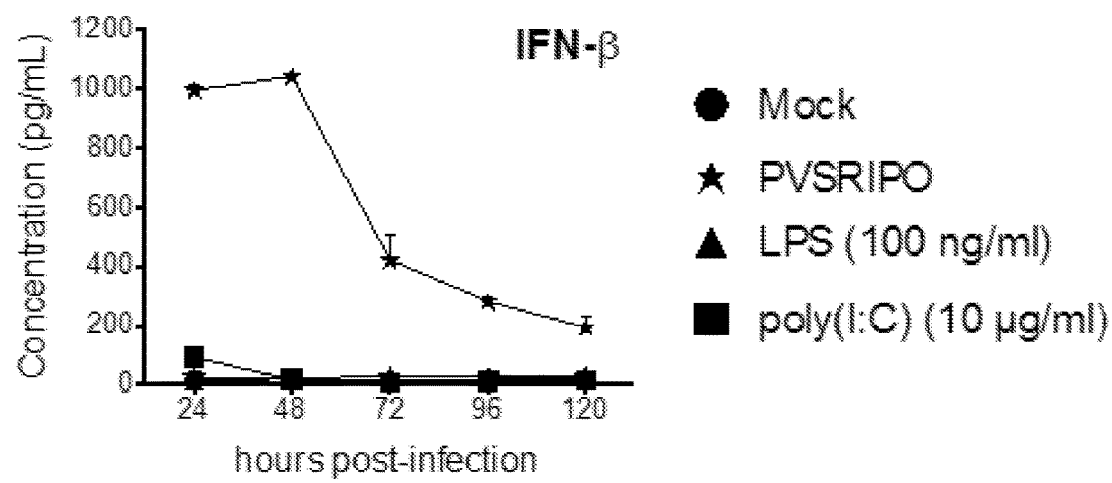
FIG. 3B is a graph showing the concentration of IFN-β secreted by human dendritic cells, as measured by ELISA, at 8, 24, 48, 72, 86, and 120 hours following no treatment (M, ●), or treatment with chimeric poliovirus (PVRIPO, ★) or LPS (▲), or poly(I:C) ("pIC," ■).
Figure 3C:
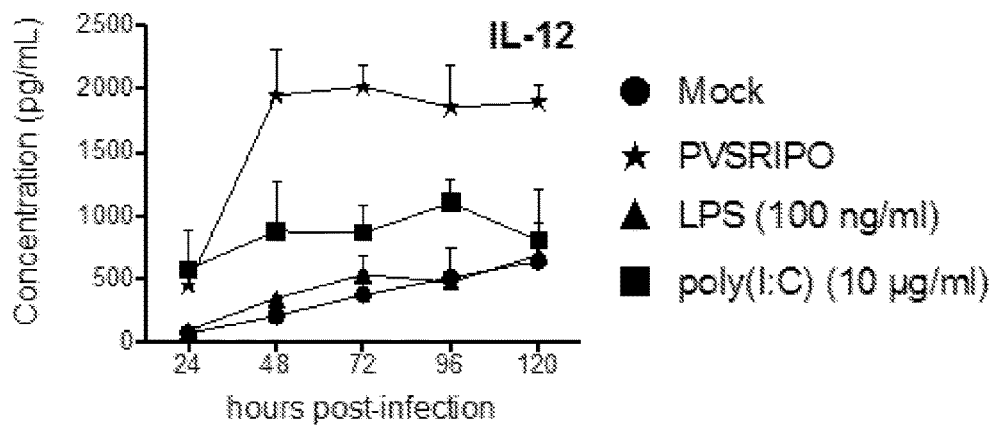
FIG. 3C is a graph showing the concentration of IL-12 secreted by human dendritic cells, as measured by ELISA, at 8, 24, 48, 72, 86, and 120 hours following no treatment (M, ●), or treatment with chimeric poliovirus (PVRIPO, ★) or LPS (▲), or poly(I:C) ("pIC," ■).
Figure 3D:
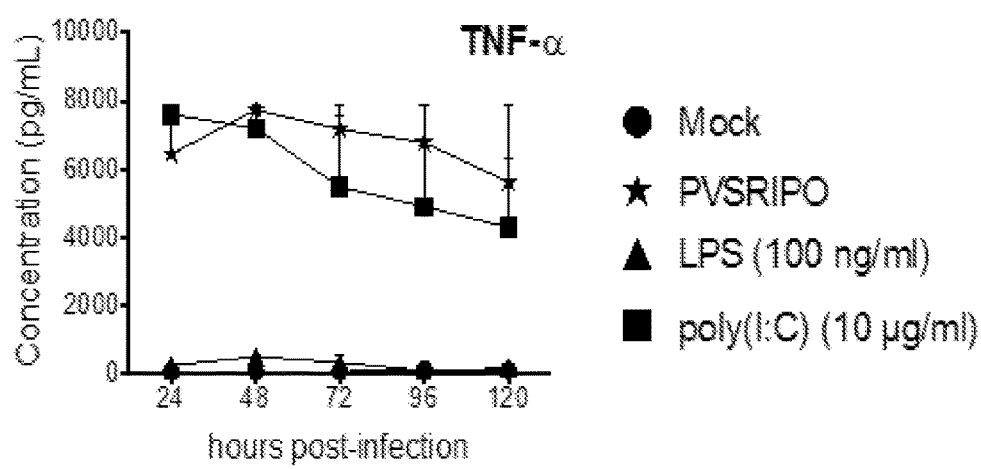
FIG. 3D is a graph showing the concentration of TNF-α secreted by human dendritic cells, as measured by ELISA, at 8, 24, 48, 72, 86, and 120 hours following no treatment (M, ●), or treatment with chimeric poliovirus (PVRIPO, ★) or LPS (▲), or poly(I:C) ("pIC," ●).
Figure 3E:
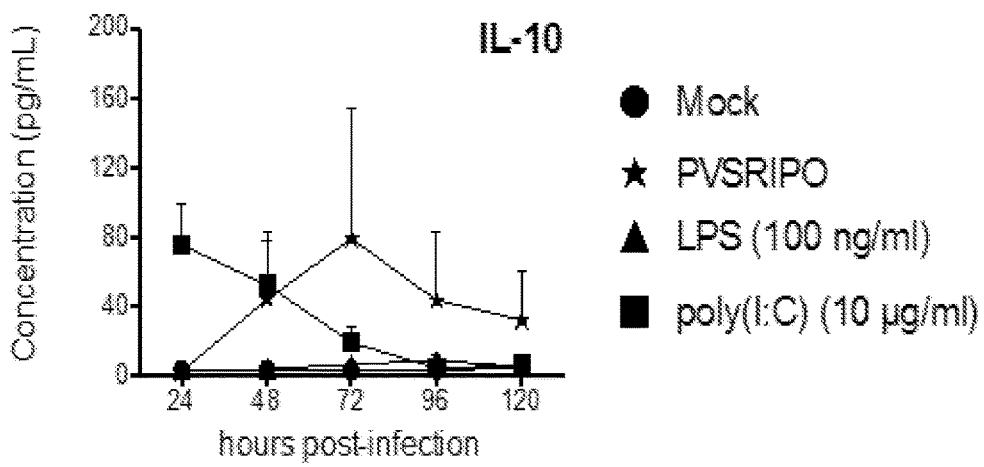
FIG. 3E is a graph showing the concentration of IL-10 secreted by human dendritic cells, as measured by ELISA, at 8, 24, 48, 72, 86, and 120 hours following no treatment (M, ●), or treatment with chimeric poliovirus (PVRIPO, ★) or LPS (▲), or poly(I:C) ("pIC," ■).
Figure 4A:
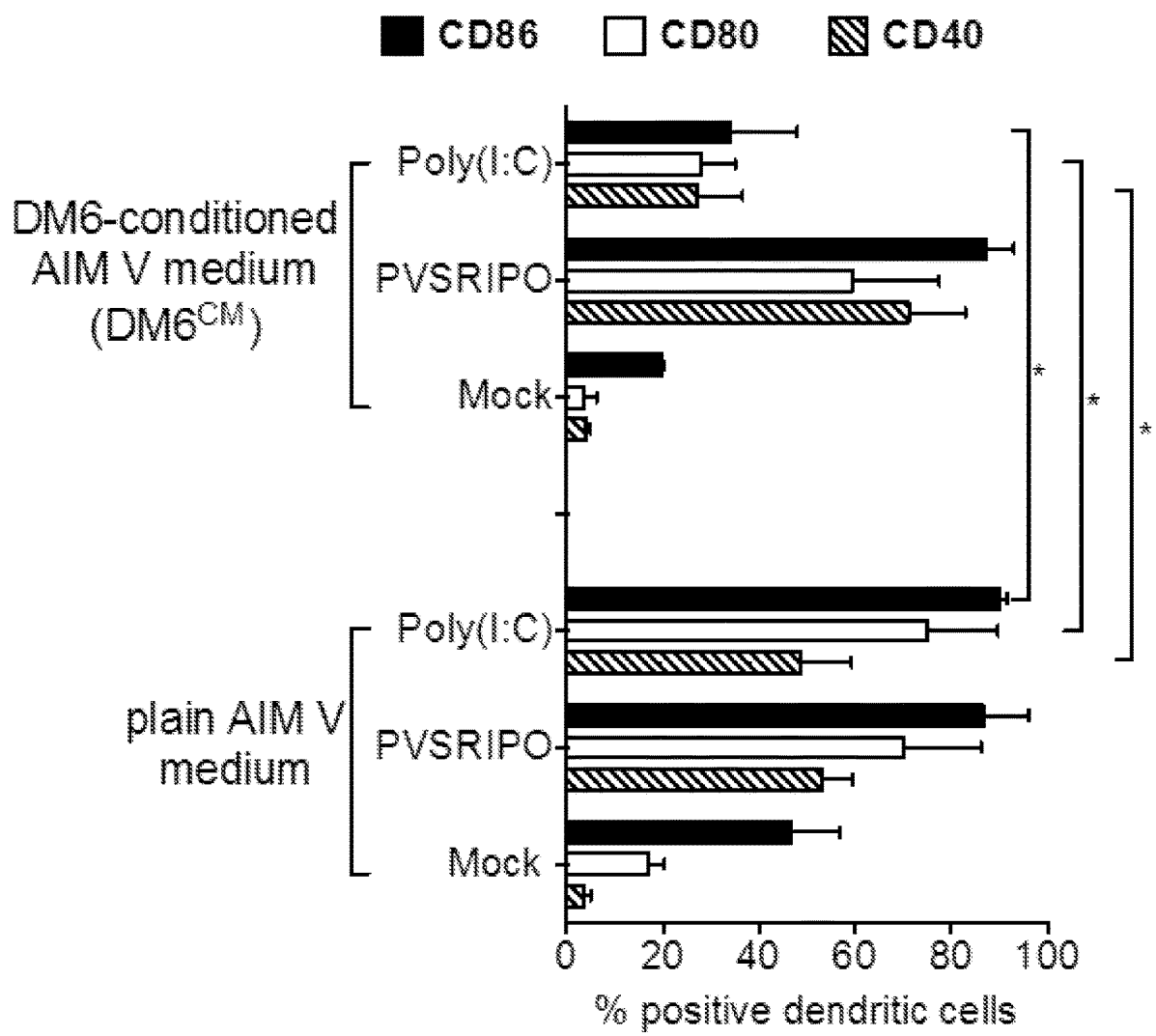
FIG. 4A is a bar graph showing the percent dendritic cells expressing cell activation markers CD86 (solid black bar), CD80 (white bar), and CD40 (hatched bar) by human dendritic cells incubated for 48 hours in cell culture medium harvested from DM6 melanoma cells ($DM6^{CM}$) or cell culture medium alone which were then either not treated (Mock), or treated with chimeric poliovirus (PVSRIPO), or Poly(I:C).
Figure 4B:
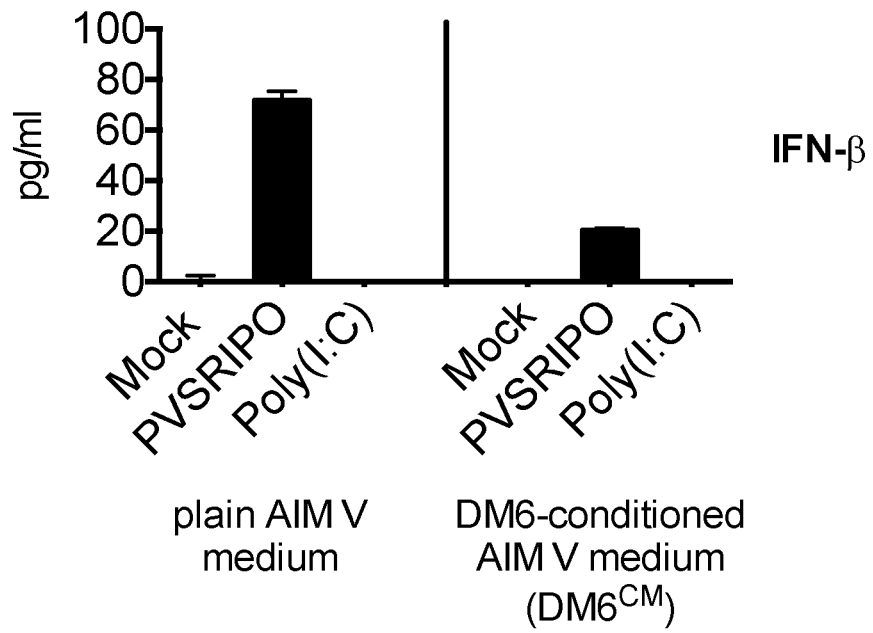
FIG. 4B is a bar graph showing the amount of IFN-β secreted, as measured by ELISA, from human dendritic cells incubated for 48 hours in cell culture medium harvested from DM6 melanoma cells ($DM6^{CM}$) or cell culture medium alone which were then either not treated (Mock), or treated with chimeric poliovirus (PVSRIPO), or Poly(I:C).
Figure 4C:
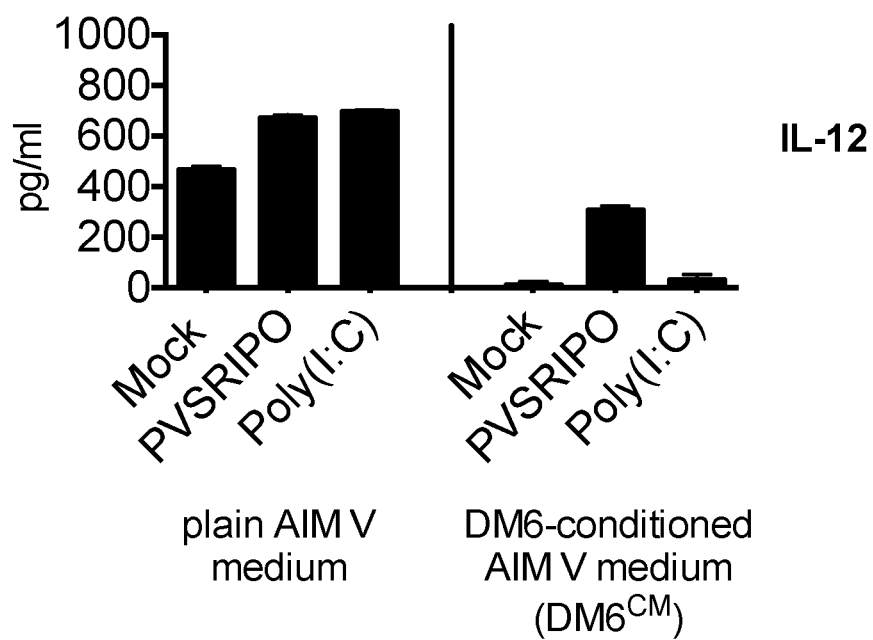
FIG. 4C is a bar graph showing the amount of IL-12 secreted, as measured by ELISA, by human dendritic cells incubated for 48 hours in cell culture medium harvested from DM6 melanoma cells ($DM6^{CM}$) or cell culture medium alone which were then either not treated (Mock), or treated with chimeric poliovirus (PVSRIPO), or Poly(I:C).
Figure 4D:
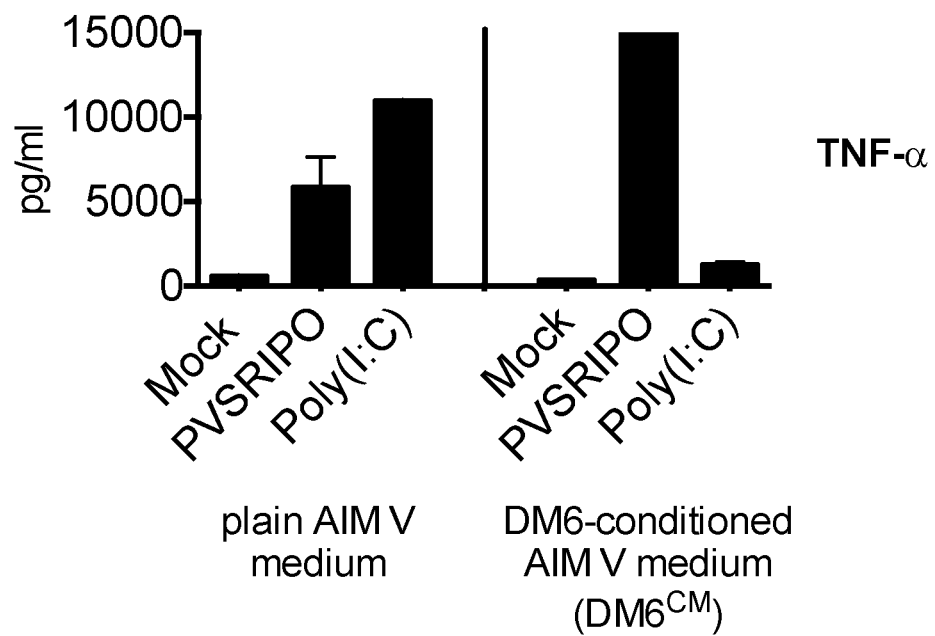
FIG. 4D is a bar graph showing the amount of TNF-α secreted, as measured by ELISA, from human dendritic cells incubated for 48 hours in cell culture medium harvested from DM6 melanoma cells ($DM6^{CM}$) or cell culture medium alone which were then either not treated (Mock), or treated with chimeric poliovirus (PVSRIPO), or Poly(I:C).
Figure 5A:
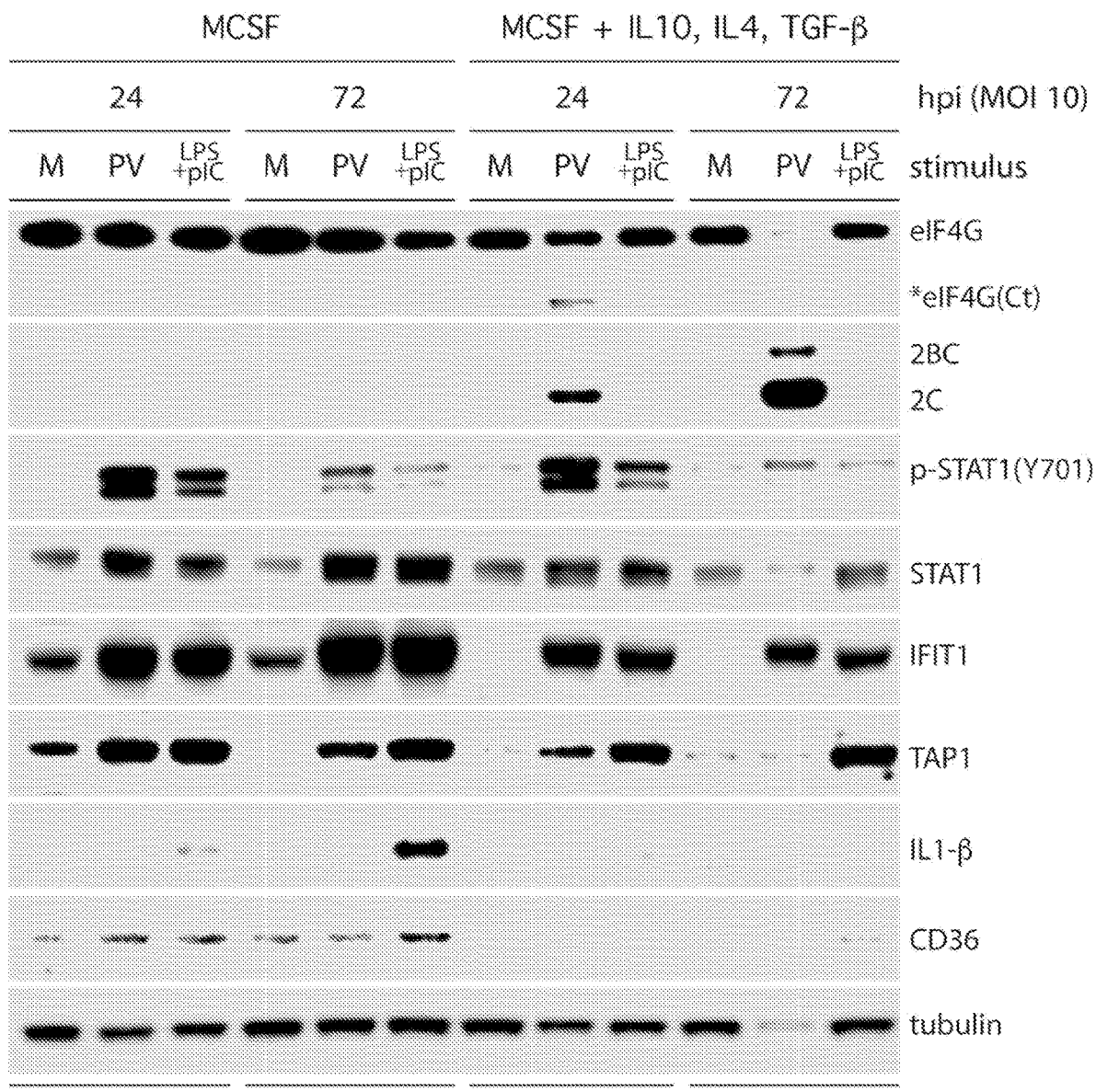
FIG. 5A is an immunoblot of lysates of macrophages differentiated in macrophage colony-stimulating factor ("MCSF") alone or with MCSF+IL10, IL4, TGF-β showing expression of various proteins (eIF4G, *eIF4G(Ct), 2BC, 2C, MDA5, p-STAT1(Y701), STAT1, IFIT1, TAP1, IL1-β, CD36, and tubulin) at 24 hours and 72 hours following no treatment (M), or treatment with chimeric poliovirus ("PV"; MOI=10), or a combination of LPS (100 ng/ml) and poly (I:C) (10 μg/ml) ("LPS+pIC).
Figure 5B:
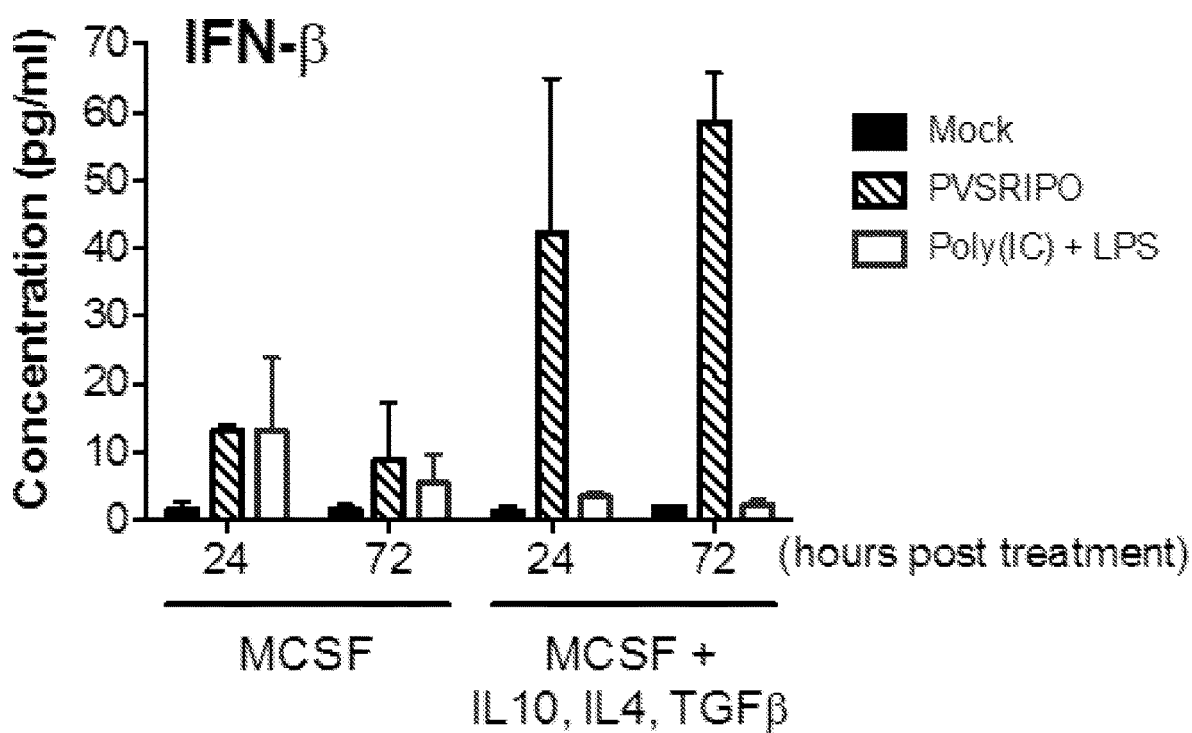
FIG. 5B is a bar graph showing the amount of IFN-β secreted, as measured by ELISA, from macrophages differentiated in macrophage colony-stimulating factor ("MCSF") alone or with MCSF+ IL10, IL4, TGF-β at 24 hours and 72 hours following no treatment ("Mock"; black bar), or treatment with chimeric poliovirus ("PVSRIPO"; MOI=10; hatched bar), or a combination of LPS (100 ng/ml) and poly(I:C) (10 μg/ml) ("Poly(IC)+LPS"; white bar).
Figure 5C:
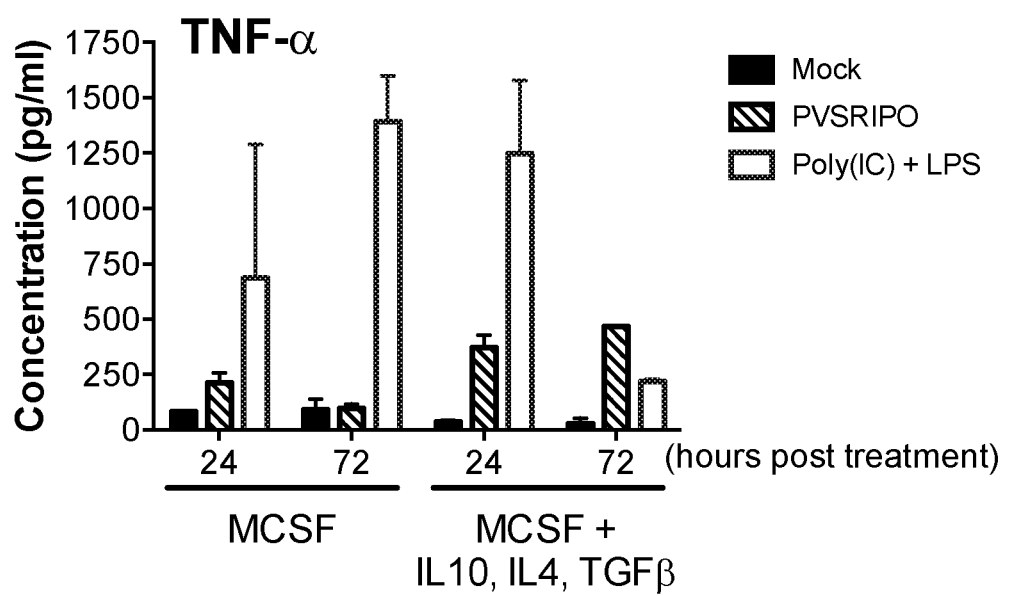
FIG. 5C is a bar graph showing the amount of TNF-α secreted, as measured by ELISA, from macrophages differentiated in macrophage colony-stimulating factor ("MCSF") alone or with MCSF+IL10, IL4, TGF-β at 24 hours and 72 hours following no treatment ("Mock"; black bar), or treatment with chimeric poliovirus ("PVSRIPO"; MOI=10; hatched bar), or a combination of LPS (100 ng/ml) and poly(I:C) (10 μg/ml) ("Poly(IC)+LPS"; white bar).

As shown in FIG. 2A, and as measured by LDH release, infection of CD155+ human tumor cells (▲, ▼) resulted in cell death and lysis, whereas infection of human dendritic cells (■, ●) showed no evidence of cell death or lysis. As shown in FIG. 2B, infection of CD155+ human tumor cells (▲, ▼) resulted in production of infectious chimeric poliovirus, whereas infection of human dendritic cells (■) showed minimal production of infectious chimeric poliovirus. The human DCs infected with chimeric poliovirus were then subjected to gel electrophoresis and immunoblotting. As shown in FIG. 2C, rather than viral cytotoxicity, the most prominent effect of infection of DCs by chimeric poliovirus was a robust, durable type I interferon (IFN) response, indicated by STAT1(Y701) phosphorylation with STAT1 and IFN-stimulated gene (ISG) induction (IFIT1, ISG15; FIG. 2C). Also observed was a substantial upregulation of TAP1 (FIG. 2C), a protein required for MHC class I-restricted antigen processing in cells, which is inducible by IFN-β. These changes, indicative of an enhanced DC activation status, were also accompanied by induction of CD40 (FIG. 2C). Upregulation of cell-surface receptors on chimeric poliovirus-infected DCs that act as co-receptors in T-cell activation (such as CD80, CD86, and CD40) greatly enhancing the ability of these activated DCs to activate T-cells in inducing an immune response.

Demonstrated herein is that, unexpectedly, infection of DCs with chimeric poliovirus (e.g., PVSRIPO) does not result in a lethal infection, and further infection of DCs with chimeric poliovirus resulted in activation of the infected DCs, via a type I IFN response.

EXAMPLE 2

Activation of antigen-presenting cells by chimeric poliovirus. In addition to the evidence presented in the Example 1 here, illustrated in this example is additional evidence of activation of DCs infected with chimeric poliovirus. DCs are professional antigen presenting cells capable of stimulating naive immune cells to produce antigen-specific immune responses. Accordingly, either in vivo or ex vivo activation of DCs has been shown to potentiate the success of vaccination strategies. Factors that determine the success of DC vaccines or immunogenic compositions include the longevity of DC activation/inflammation, as well as the type of DC activation (e.g., for promoting a Th2 immune response or Th1 immune response). Current standard methods for activation of DCs involve exposure to either cytokine cocktails; TLR agonists such as Poly (I:C), a double stranded RNA mimetic that activates TLR3; or lipopolysaccharide (LPS), a bacterial cell wall component that activates TLR4. These methods may be suboptimal in inducing immune responses because they artificially activate only one innate receptor without providing the additional inflammatory context coincident with a pathogen infection, and because they only transiently induce DC activation.

The adjuvant effect of chimeric poliovirus on DCs was compared with standard methods of maturing and activating human immature DCs via TLR-stimulation pathways with lipopolysaccharide (LPS), poly(I:C), or with maturation cytokine cocktail that is used in clinical applications of DC-based vaccines. For this comparison, immature human dendritic cells were untreated (mock) or treated with chimeric poliovirus (PVSRIPO; MOI=10), or LPS (100 ng/ml), or poly(I:C) (10 μg/ml), or maturation cytokine cocktail (TNF-α, 10 ng/ml; IL-1β, 10 ng/ml; IL-6, 1000 U/ml; and $PGE_2$, 1 μg/ml). Cells and supernatant were harvested at 24, 48, 72, 96, and 120 post-treatment. Cell lysates were analyzed by immunoblot for the IFN response and DC activation proteins. Enzyme-linked immunoassays (ELISA) were used to measure IFN-β, TNF-α, IL-12, and IL-10 in DC supernatants post-treatment (data representing cumulative cytokine release at the designated time points). As shown in FIG. 3A, compared to treatment of the DCs with TLR stimuli (LPS and poly (I:C), "pIC")), or mock-treated cells ("M"), or cells treated with the maturation cytokine cocktail ("CC"), infection of DCs by chimeric poliovirus ("PV") was distinguished by potent, sustained STAT1(Y701)-phosphorylation and induction of interferon-stimulated genes throughout the 5-day period of measurement. As shown in FIG. 3B, the potent type 1 interferon response coincided with IFN-β release at levels exceeding all other agents tested in activating DCs, as IFN-β release was either minimal or undetectable in DCs treated with Poly(I:C), or LPS. Chimeric poliovirus infection of DCs also led to higher levels and sustained production of IL-12 (FIG. 3C) and TNF-α (FIG. 3D), as well as higher levels of IL-10 (FIG. 3E) relative to DCs mock-treated or treated with poly(I:C) or LPS. Note that CC-stimulated DCs were not assayed for cytokine production in this experiment, because the cocktail contains TNF-α; however, FIG. 3A shows the DCs treated with the cytokine cocktail ("CC") lack the ability to induce type I IFN activity.

Activation of Antigen Presenting Cells in an immunosuppressive environment. Pathogens can impair immature DCs by interference with DC maturation. For example, herpes simplex virus type 1 (HSV-1) infection of immature human DCs in vitro has been shown to inhibit their maturation and, hence, their ability to induce an antiviral immune response. Similarly, parasites can interfere with DC maturation. For example, erythrocytes infected with the malaria parasite *Plasmodium falciparum* modulate the maturation of DCs and, hence, their ability to activate T cells in an anti-parasite immune response. Also, DC responses to *Borrelia* spirochetes are affected by tick cystatins which influences the maturation of DC and, thus, impair an adaptive immune response. Dendritic cell activation is also hampered in the immunosuppressive context of the tumor microenvironment. In this example, chimeric poliovirus (PVSRIPO) was compared to poly(I:C) in terms of their ability to activate immature DCs that have been subjected to immunosuppressive conditions.

Human immature dendritic cells were cultured for 24 hours in culture medium alone or in cancer cell-conditioned medium (cell culture medium harvested from DM6 melanoma cells after 48 hours in culture; "$DM6^{CM}$"). $DM6^{CM}$ contained a range of cytokines implicated in suppression of antigen presenting cells and other immune cell functions including VEGF-A, M-CSF, CCL2 CXCL1, and soluble IL-6R. Immature DCs incubated in $DM6^{CM}$ showed reduced basal levels of CD40, CD80, CD86 as compared to immature DCs incubated in cell culture medium alone. Despite such immunosuppression of dendritic cell activation and maturation, $DM6^{CM}$-exposed immature DCs infected with chimeric poliovirus showed enhanced expression of activation markers CD40, CD80, and CD86 at levels comparable those induced by immature dendritic cells cultured in cell culture medium alone ("plain AIM V medium") and infected with chimeric poliovirus ("PVSRIPO") (FIG. 4A). In contrast, expression of CD40, CD80, and CDβ86 upon poly(I:C) treatment was markedly reduced in $DM6^{CM}$-cultured DCs compared immature DCs cultured in cell culture medium alone and treated with poly(I:C) (FIG. 4A). Only infection of immature DCs with chimeric poliovirus, but not poly(I:C) stimulation, led to potent, sustained IFN-β release in DM6$^{CM}$-exposed immature DCs (FIG. 4B). Interestingly, DCs cultured in DM6$^{CM}$ did not produce significant amounts of IFN-β (FIG. 4B), IL-12 (FIG. 4C), or TNF-α (FIG. 4D) after poly(I:C) treatment, but retained IFN-β (FIG. 4B), IL-12 (FIG. 4C), or TNF-α (FIG. 4D) release after chimeric poliovirus infection. While chimeric poliovirus infection induced IFN-β and IL-12 production was tempered in DM6$^{CM}$-cultured DCs, compared to production by DCs exposed to cell culture medium alone and infected with chimeric poliovirus, TNF-α production was actually enhanced in immunosuppressive conditions (FIG. 4D). These data suggest that while immunosuppressed DCs are resistant to poly(I:C) stimulation, they retain sensitivity to activation mediated by infection with chimeric poliovirus. In other words, chimeric poliovirus activates DCs, even in the presence of immunosuppression.

Pathogens as well as tumors can induce immunosuppression of other antigen presenting cells, such as macrophages. For example, *Borrelia* can desensitize human macrophages to activation stimuli through TLR receptors, in part due to induction of IL-10 production. Macrophage activation is also suppressed in malarial infection, contributing to the immunosuppression observed in humans with malaria. Tumor-associated macrophages are implicated in tumor immunosuppression. Investigated were the effects of chimeric poliovirus (e.g., PVSRIPO) infection on macrophages in vitro.

Purified human monocytes (isolated from PBMCs) were differentiated to macrophages with a macrophage colony-stimulating factor (MCSF; 25 ng/ml) alone, or with MCSF plus TGF-β, IL-10 and IL-4 (all at 20 ng/ml) for seven days. These additional cytokines induce an immunosuppressive phenotype in vitro, associated with reduced basal expression of IFIT1, TAP1, and CD36, a scavenger receptor associated with macrophage activity. The macrophages were treated with chimeric poliovirus (MOI of 10) or treated with a combination of LPS (100 ng/ml) and poly (I:C) (10 μg/ml) for either 24 hours or 72 hours. As in DCs, infection of macrophages with chimeric poliovirus ("PV") yielded robust type-I IFN responses (FIGS. 5A & B) and TNF-α production (FIG. 5C) that was paradoxically enhanced in the immunosuppressed macrophages (FIGS. 5B and 5C, MCSF +IL10, IL4, TGF-β) that were then infected with chimeric poliovirus. Viral translation or cytopathogenicity were not detected in chimeric poliovirus-infected macrophages derived with MCSF only (FIG. 5A), but increased IFN-β release (FIG. 5B) in immunosuppressed macrophages correlated with enhanced viral translation and overt cytopathogenicity (FIG. 5A, eIF4G cleavage, tubulin loss) upon prolonged infection. Treatment of macrophages with combined poly(I:C) and LPS ("Poly(IC)+LPS") induced IL1-β (FIG. 5A), IFN-β (FIG. 5B), and TNF-α responses (FIG. 5C) in MCSF-derived macrophages. However, in comparison to macrophages treated with combined Poly(I:C)+LPS at 72 hours, treatment of immunosuppressed macrophages, with combined Poly(I:C)+LPS at 72 hours resulted in reduced IL1-β (FIG. 5A), IFN-β (FIG. 5B), and TNF-α production (FIG. 5C). Analysis of human monocytes without differentiation revealed similar type-I IFN responses to chimeric poliovirus infection as in MCSF-derived macrophages. These findings suggest that chimeric poliovirus infection of macrophages (and monocytes) yields type I IFN-dominant activation that is—paradoxically—enhanced by an immunosuppressive macrophage phenotype. In other words, chimeric poliovirus activates macrophages, even in the presence of immunosuppression.

EXAMPLE 3

This example illustrates use of activated DCs in promoting an immune response. An antigen may be contacted with DCs simultaneous, concurrent, or sequential to activation with chimeric poliovirus. Techniques for loading of an antigen into DCs are known to those skilled in the art to include, but are not limited to, pulsing (through incubation with) dendritic cells with antigen (e.g., purified antigen or cell lysate containing antigen); electroporating, transfecting, transducing or otherwise introducing DNA or RNA or mRNA encoding antigen; or immune complex loading (antigen bound to antibody having binding specificity therefor).

Preparation of RNA encoding an immunogenic agent. pSP73-Sph/A64 was generated by adding oligonucleotides containing 64 A-T base pairs followed by an SpeI restriction site placed between the EcoRI and NarI sites of pGEM4Z to create the plasmid pGEM4Z/A64. The HindIII-NdeI fragment of pGEM4Z/A64 was cloned into pSP73, digested with HindIII and NdeI to create pSP73/A64. pSP73-Sph was created by digesting pSP73/A64 with SphI, filling in the ends with T4 DNA polymerase, followed by re-ligation. pSP73-Sph/A64/Not contains a NotI restriction site adjacent to the SpeI site. Open reading frames (ORFs) encoding the full-length tumor antigen (PSA, MART-A27L and CEA) were inserted into the pSP73-Sph/A64 plasmid using polymerase chain reaction (PCR) cloning. To produce cDNA encoding MART-1 with an A27L mutation, the native MART-1 DNA was used as a DNA template. Overlapping PCR was performed to substitute the codon encoding amino acid #27 from GCC alanine to CTC leucine. The amplified overlapping mutated PCR product was then cloned into the pSP73-Sph/A64 plasmid. The ORF encoding the tumor antigen EGFR was inserted into the pcDNA3.1/A64 plasmid using PCR cloning. This modified pcDNA3.1 plasmid contains a T7 promoter 5' to the insert site into which a 64-adenosine synthetic poly(A) tail segment was inserted at the 3' end of the multiple cloning site. A SpeI restriction site is located at the 3' end of the 64-adenosine segment of pcDNA3.1/A64 plasmid for linearization of the DNA prior to in vitro RNA transcription. RNA was produced using a commercially available kit following the manufacturer's instructions using SpeI linearized plasmids; mRNA was purified with a commercially available mini kit. Cloning and generation of mRNA that encodes the tumor antigen TRP-2, OVA and GFP was performed using similar methods.

Antigen loading using electroporation of mRNA. DCs ($2\times10^6$) suspended in 200 μl culture medium were mixed with 25 μg/ml in-vitro-transcribed RNAs in 2-mm cuvettes and were electroporated at 340 V for 500 μs using an electroporator.

Antigen loading by pulsing with immunogenic agent. In this illustration, used were human CD155+, HLA-A2+, MHC class I-expressing tumor cell lines SUM149 inflammatory breast cancer, MDA-MB231 triple-negative breast cancer, DM6 melanoma and LNCaP prostate cancer. Cancer cell lysates (oncolysates) for use in loading DCs were prepared by adding virus to a 75% confluent 100 mm dish in cell culture medium (MOI=0.1), incubation for 48 hours, followed by centrifugation to remove cell debris, and to collect the supernatant for treating DCs. Mock controls were generated similarly, only without virus addition. Since the chimeric poliovirus used, PVSRIPO, can infect tumor cells, replicate to produce more chimeric poliovirus, and then lyse the infected tumor cells, generated is a tumor cell lysate containing chimeric poliovirus. To generate chimeric poliovirus oncolysate-loaded DCs, 1 ml of lysate was added to $1\times10^6$ immature DCs followed by incubation for 24 hours in culture.

Induction of an immune response by antigen loaded, activated antigen presenting cells. Human DCs exposed to chimeric poliovirus-containing oncolysate were examined for the ability to load tumor antigen in a cell lysate (e.g., oncolysate), present it, and prime autologous T cells using an in vitro DC-T cell stimulation assay. For in vitro stimulation of T cells with DCs treated with PVSRIPO oncolysate, PBMCs were thawed, incubated for 1 hour, and non-adherent cells were harvested. The non-adherent cells were then stimulated with DCs loaded with chimeric poliovirus-induced oncolysate at a responder cell to stimulator DC ratio of 10:1 in the presence of 25 ng/ml IL-7. All stimulations were done in RPMI 1640 with 10% FCS, 2 mM L-glutamine, 20 mM HEPES, 1 mM sodium pyruvate, 0.1 mM MEM non-essential amino acids, 100 IU/ml penicillin, 100 μg/ml streptomycin and $5\times10^{-5}$ M β-mercaptoethanol (cytotoxic T lymphocyte (CTL) stimulation medium). The responder cell concentration was $2\times10^6$ cells/ml. IL-2 was added at 100 U/ml on day 3 and at 50 U/ml every 4-5 days. T cells were maintained at $1\text{-}2\times10^6$ cells/ml in CTL stimulation medium. In some assays, T cells were re-stimulated with chimeric poliovirus-containing oncolysate loaded DCs at a responder to stimulator ratio of 10:1 after 7 days. T cells were harvested on day 12-14, counted and used as effector cells in a CTL assay. In the CTL assay, aforementioned human tumor cell lines and RNA-electroporated DCs were used as targets. Cells were harvested, washed to remove all traces of media and then were europium (Eu)-labeled using methods known in the art. Ten-thousand Eu-labeled targets (T) and serial dilutions of effector cells (E) at varying E:T ratios were incubated in 200 μl of CTL stimulation medium without antibiotics in 96-well V-bottom plates. The plates were centrifuged and incubated for 4 hours. Supernatant (50 μl) was harvested and added to enhancement solution (150 μl; an acidic chelating detergent solution intended for use in the quantitative determination of $Eu^{3+}$) in 96-well flat-bottom plates and Eu-release was measured by time resolved fluorescence using the VICTOR3 Multilabel Counter (Perkin-Elmer). Specific cytotoxic activity was determined using the formula:

% specific release=[(experimental release−spontaneous release)/(total release−spontaneous release)]×100.

Spontaneous release in target cells was <25% of total release by detergent. Spontaneous release in target cells was determined by incubating the target cells in medium without T cells. After 12-14 days of DC:T cell co-culture in vitro, the cells were harvested and assayed for tumor antigen-specific cytotoxic reactivity using the standard 4 hour europium (Eu)-release CTL assay described above. To assess CTL reactivity, T cells (effectors) were cultured with the following Eu-labeled target cells: (i) the tumor cell line yielding the chimeric poliovirus-containing oncolysate used for DC loading; (ii) DCs transfected with mRNA encoding a tumor antigen known to be expressed by the tumor cell line (assay positive control); or (iii) DCs transfected with mRNA encoding an irrelevant tumor antigen not expressed by the tumor cell line (assay negative control). The use of autologous antigen-expressing DCs as positive and negative control targets allowed determination of specific CTL reactivity to known tumor antigens, by eliminating MHC mismatch between T cells and targets cells. CTL-mediated killing of the target cells was assessed by measuring Eu-release in the supernatant.

Figure 6A:
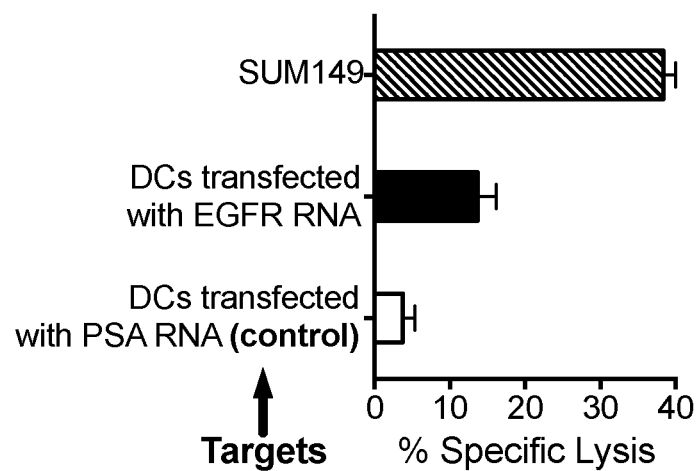
FIG. 6A is a bar graph showing the percent lysis of SUM149 human tumor cells (hatched bar), autologous human dendritic cells ("DCs") transfected with EGFR RNA (positive control; (black bar)), and autologous human dendritic cells ("DCs") transfected with PSA RNA (negative control; (white bar)) as mediated by autologous (with respect to the dendritic cells) or MHC-matched (with respect to tumor cells) effector human T cells stimulated with SM149 oncolysate-pulsed autologous DCs.
Figure 6B:
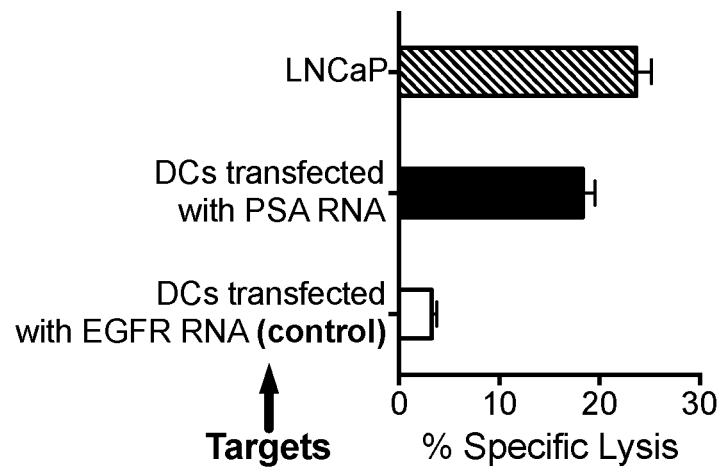
FIG. 6B is a bar graph showing the percent lysis of LNCaP human tumor cells (hatched bar), autologous human dendritic cells ("DCs") transfected with PSA RNA (positive control; (black bar)), and autologous human dendritic cells ("DCs") transfected with EGFR RNA (negative control; (white bar)) as mediated by autologous (with respect to the dendritic cells) or MHC-matched (with respect to tumor cells) effector human T cells stimulated with LNCaP oncolysate-pulsed autologous DCs.
Figure 6C:
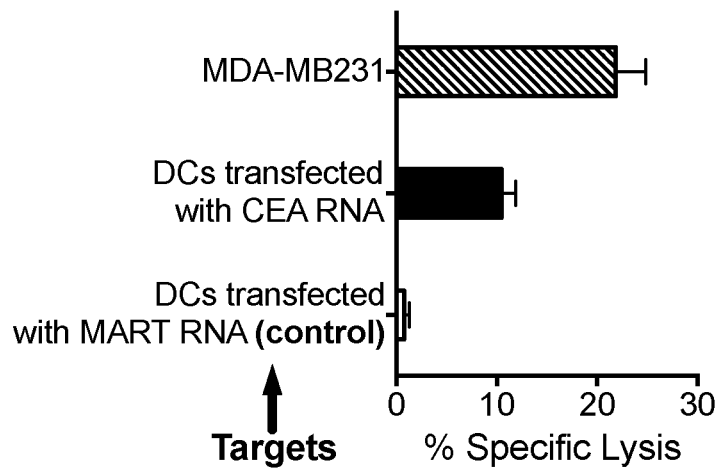
FIG. 6C is a bar graph showing the percent lysis of MDA-MB231 human tumor cells (hatched bar), autologous human dendritic cells ("DCs") transfected with CEA RNA (positive control; (black bar)), and autologous human dendritic cells ("DCs") transfected with MART RNA (negative control; (white bar)) as mediated by autologous (with respect to the dendritic cells) or MHC-matched (with respect to tumor cells) effector human T cells stimulated with MDA-MB231 oncolysate-pulsed autologous DCs.
Figure 6D:
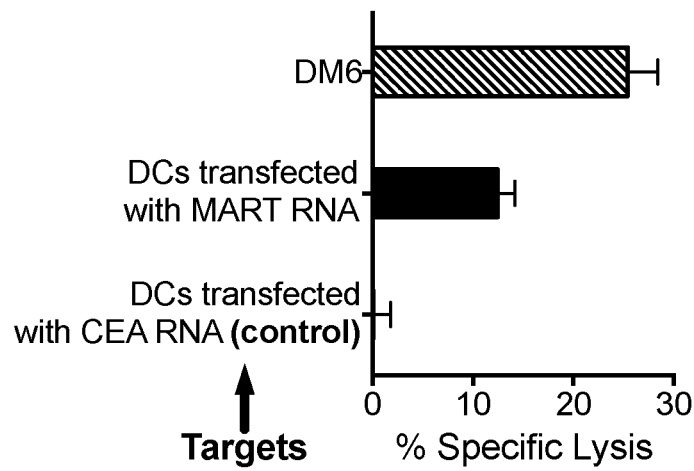
FIG. 6D is a bar graph showing the percent lysis of DM6 human tumor cells (hatched bar), autologous human dendritic cells ("DCs") transfected with MART RNA (positive control; (black bar)), and autologous human dendritic cells ("DCs") transfected with CEA RNA (negative control; (white bar)) as mediated by autologous (with respect to the dendritic cells) or MHC-matched (with respect to tumor cells) effector human T cells stimulated with SM149 oncolysate-pulsed autologous DCs.

T cells were co-cultured with oncolysate-pulsed autologous DCs and the stimulated effector T cells were then harvested and tested in a CTL assay against the corresponding tumor cells (FIGS. 6A-D; hatched bars), autologous DCs transfected with RNA that encodes for a relevant tumor antigen (FIGS. 6A-D; black bars; positive control), autologous DCs transfected with RNA that encodes for an irrelevant tumor antigen as relating to the targeted tumor (FIG. 6A. PSA; FIG. 6B, EGFR; FIG. 6C, MART; and FIG. 6D, CEA; white bars; negative control). Each bar represents average % specific lysis and standard deviation (SD) of triplicate samples. Statistical significance comparing autologous DCs expressing either the relevant or irrelevant tumor antigen for each of FIGS. 6A-D was done using paired two-tailed Student's t test. A probability of less than 0.05 (p<0.05) is considered statistically significant: FIG. 6A, SUM149 DC targets, p=0.04; FIG. 6B, LNCaP DC targets, p=0.0008; FIG. 6C, MDA-MB231 DC targets, p=0.01; and FIG. 6D, DM6 DC targets, p=0.01. DCs treated with chimeric poliovirus-containing oncolysate produced CTL responses that effectively lysed the original cancer lines (FIGS. 6A-D, hatched bars) as well as the positive control (DCs expressing a relevant tumor antigen; FIGS. 6A-D, black bars), but not the negative control (DCs expressing an irrelevant tumor antigen; FIGS. 6A-D, white bars). Remarkably, antigen presentation by chimeric poliovirus-containing oncolysate-treated DCs did not require the additional maturation step with the cytokine-cocktail (CC), which is required and routinely used to stimulate effector T cells in such in vitro assays. The conclusion is that DC maturation/activation in this instance was due to infection of DCs with chimeric poliovirus present in the oncolysate. Since the oncolysate represents the entire repertoire of tumor-antigens of a tumor, oncolysate-stimulated T cells likely target multiple tumor antigens, which may explain higher levels of tumor cell lysis versus target DCs expressing only 1 selected tumor antigen. Of note, SUM149 breast cancer oncolysate-stimulated T cells did not lyse LNCaP prostate cancer cells and vice-versa Moreover, DCs loaded with supernatant from mock-infected cells did not stimulate antigen-specific T cells as indicated by minimal lysis of target cells.

Together, these findings indicate that chimeric poliovirus-infected and activated APCs: (1) induce co-stimulatory molecule expression; (2) can be loaded with an antigen, with antigen processing and presentation; and (3) can induce an immune response against such antigen, including mediating T cell cytotoxicity against cells expressing such antigen.

EXAMPLE 4

Illustrated in this example are uses of compositions and methods provided herein. Compositions provided herein include (a) an isolated immunogenic composition comprising a chimeric poliovirus and an antigen; (b) antigen presenting cells (e.g., dendritic cells or macrophages) activated with chimeric poliovirus (e.g., ex vivo or dermal); and (c) antigen presenting cells activated with chimeric poliovirus and loaded with an antigen (e.g., ex vivo, or dermal). Any of these compositions may be used in a method of treating an individual. Specifically, where antigen in the composition comprises a tumor antigen, such composition may be used to treat an individual that has tumor, is suspected of having tumor, or is at high risk (e.g., as determined by genetic tests for predictive risk) of developing tumor.

Specifically, where antigen in the composition comprises a pathogen antigen, such composition may be used in methods of treating (therapeutically or prophylactically) pathogenic infections, for example parasitic, bacterial, or viral infections. For example, the composition may be administered prior to infection to elicit a protective immune response in the individual, or after infection to stimulate the individual's immune system to induce an immune response for fighting the infection.

For administering a composition, the composition may further comprise a pharmaceutically acceptable carrier to produce a pharmaceutical composition or medicament. In one aspect where the composition comprises a dendritic cell as a component of the composition, dendritic cells are first isolated from the tissue or body fluid that contains the desired dendritic cells, and then the isolated dendritic cells are contacted with either chimeric poliovirus, or chimeric poliovirus and antigen. The resultant activated dendritic cells may then be administered to an individual in need of treatment by a method of administration known in the art; e.g., dermal. Intradermal, intramuscular, subcutaneous, intravenous, intranasal, or by direct injection into the lymph nodes. The desired or optimal route of administration and amount to be administered can be determined by a skilled practitioner for any particular individual to be treated depending on, for example, the age, weight, immune status, and health of the individual to be treated as well as the disease to be treated.

In one aspect, a composition provided herein may be used as a dermal vaccine formulation that is designed for targeted delivery of the antigen preferably, selectively and specifically, to the intradermal compartment of an individual's skin. Thus, in one aspect, an immunogenic composition is targeted directly to the intradermal compartment of skin. The adjuvant component in the immunogenic composition, comprising chimeric poliovirus, activates antigen presenting cells which, when contacted with the antigen component of the immunogenic composition, enhances the presentation and/or availability of the antigen to immune cells, in eliciting an immune response against the antigen. A pharmaceutical composition or medicament which comprises an immunogenic composition for administration dermally may further comprise a composition for enhancing the effectiveness of the immunogenic composition, such composition consisting of an agent for creating a depot effect, or a penetration enhancer. An agent for creating a depot effect slows the release of one or more components in the immunogenic composition at the site of administration so as to prolong exposure of the one or more components of the immunogenic composition to antigen presenting cells at the site of administration, e.g., a dermal compartment, which may potentiate the immune response elicited. Such compositions are known to those skilled in the art to include oils, viscous substances, gels, and polymers. A penetration enhancer is any molecule that may be used to promote absorption into a dermal compartment or enhance permeability or transfer of the immunogenic composition into or across one or more dermal compartments of the skin to reach the desired site of delivery of the immunogenic composition. Penetrants or penetration enhancers are known to those skilled in the art to include, but are not limited to, fatty acids, polymers, bile salts, and detergents.

A delivery device for administering an immunogenic composition provided herein to a dermal compartment may comprise a patch, syringe, microneedle-based injection, an infusion system, needless or needle-free ballistic injection system, Mantoux-type intradermal injection, or any other means for targeting the desired dermal compartment.

The invention claimed is:

1. An immunogenic composition comprising as separate components:
    an antigen selected from the group consisting of: an antigen of a bacterial pathogen, an antigen of a pathogenic parasite, an antigen of a non-polio virus, and a tumor antigen, wherein the antigen comprises a nucleic acid molecule; and
    an adjuvant comprising an infective chimeric poliovirus or RNA encoding the chimeric poliovirus.

2. The immunogenic composition according to claim 1 wherein the adjuvant comprises virus particles of the chimeric poliovirus.

3. The immunogenic composition according to claim 1 wherein the adjuvant comprises RNA encoding the chimeric poliovirus.

4. The immunogenic composition according to claim 3 wherein the RNA is mRNA.

5. The immunogenic composition according to claim 1 wherein the antigen is from a pathogen, wherein the pathogen is selected from the group consisting of bacteria, a non-polio virus, and a parasite.

6. The immunogenic composition according to claim 1 wherein the antigen is a nucleic acid encoding a tumor antigen.

7. The immunogenic composition according to claim 1 wherein the nucleic acid molecule comprises mRNA.

8. The immunogenic composition according to claim 1 wherein the antigen further comprises a protein.

9. An immunogenic composition comprising as separate components:
    an antigen selected from the group consisting of: an antigen of a bacterial pathogen, an antigen of a pathogenic parasite, an antigen of a non-polio virus, and a tumor antigen, wherein the antigen comprises a protein and the protein is bound to an antibody having binding specificity for the protein; and
    an adjuvant comprising an infective chimeric poliovirus or RNA encoding the chimeric poliovirus.

10. The immunogenic composition according to claim 1 wherein the_antigen is contained in a cell lysate.

11. The immunogenic composition according to claim 1 further comprising a pharmaceutically acceptable carrier.

12. The immunogenic composition according to claim 11 which is formulated for use in a vaccine.

13. A method of eliciting an immune response comprising administering to an individual the immunogenic composition according to claim 1.

14. The method according to claim 13 wherein the immunogenic composition is administered with a pharmaceutically acceptable carrier.

15. The method according to claim 14 wherein the immunogenic composition is administered dermally.

16. The immunogenic composition according to claim 1 wherein the infective chimeric poliovirus is PVSRIPO.

17. The immunogenic composition according to claim 5 wherein the infective chimeric poliovirus is PVSRIPO.

18. The immunogenic composition according to claim 8 wherein the infective chimeric poliovirus is PVSRIPO.

19. A kit comprising as separate components in separate containers:
    an antigen selected from the group consisting of: an antigen of a bacterial pathogen, an antigen of a pathogenic parasite, an antigen of a non-polio virus, and a tumor antigen, wherein the antigen comprises a nucleic acid molecule; and an adjuvant comprising an infective chimeric poliovirus or RNA encoding the chimeric poliovirus.

20. The kit of claim 19 further comprising a dermal administration device.

21. The kit according to claim 19 wherein the adjuvant comprises virus particles of the chimeric poliovirus.

22. The kit according to claim 19 wherein the adjuvant comprises RNA encoding the chimeric poliovirus.

23. The kit according to claim 22 wherein the RNA is mRNA.

24. The kit according to claim 19 wherein the antigen is from a pathogen, wherein the pathogen is selected from the group consisting of bacteria, a non-polio virus, and a parasite.

25. The kit according to claim 19 wherein the antigen is a nucleic acid encoding a tumor antigen.

26. The kit according to claim 19 wherein the nucleic acid molecule comprises mRNA.

27. The kit according to claim 19 wherein the antigen further comprises a protein.

28. A kit comprising as separate components in separate containers:

an antigen selected from the group consisting of: an antigen of a bacterial pathogen, an antigen of a pathogenic parasite, an antigen of a non-polio virus, and a tumor antigen wherein the antigen comprises a protein and the protein is bound to an antibody having binding specificity for the protein; and an adjuvant comprising an infective chimeric poliovirus or RNA encoding the chimeric poliovirus.

29. The kit according to claim 19 wherein the antigen is contained in a cell lysate.

30. The kit according to claim 19 wherein the infective chimeric poliovirus is PVSRIPO.

31. The composition of claim 1 wherein the infective chimeric poliovirus is a Sabin type I strain of poliovirus with a human rhinovirus type 2 internal ribosome entry site in the 5' untranslated region of the poliovirus between its cloverleaf structure and open reading frame.

32. The kit of claim 19 wherein the infective chimeric poliovirus is a Sabin type I strain of poliovirus with a human rhinovirus type 2 internal ribosome entry site in the 5' untranslated region of the poliovirus between its cloverleaf structure and open reading frame.

33. A method of eliciting an immune response comprising administering to an individual the components of the kit of claim 19.

34. A method of eliciting an immune response comprising administering to an individual the components of the kit of claim 28.

* * * * *